US008329668B2

(12) United States Patent
Stein et al.

(10) Patent No.: US 8,329,668 B2
(45) Date of Patent: Dec. 11, 2012

(54) ANTISENSE ANTIVIRAL COMPOUND AND METHOD FOR TREATING PICORNAVIRUS INFECTION

(75) Inventors: David A. Stein, Corvallis, OR (US); Cornelis A. Rijnbrand, Poway, CA (US); Patrick L. Iversen, Corvallis, OR (US); Dwight D. Weller, Corvallis, OR (US)

(73) Assignee: AVI Biopharma, Inc., Corvallis, OR (US)

( * ) Notice: Subject to any disclaimer, the term of this patent is extended or adjusted under 35 U.S.C. 154(b) by 0 days.

(21) Appl. No.: 11/518,058

(22) Filed: Sep. 8, 2006

(65) Prior Publication Data
US 2007/0129323 A1 Jun. 7, 2007

Related U.S. Application Data

(60) Provisional application No. 60/715,888, filed on Sep. 8, 2005, provisional application No. 60/800,120, filed on May 11, 2006.

(51) Int. Cl.
*C12N 15/11* (2006.01)
*C07H 21/04* (2006.01)
*C12Q 1/68* (2006.01)

(52) U.S. Cl. ............. 514/44 A; 536/24.5; 435/6.1
(58) Field of Classification Search ............ 536/24.5; 514/44; 424/436
See application file for complete search history.

(56) References Cited

U.S. PATENT DOCUMENTS

| | | | |
|---|---|---|---|
| 5,034,506 A | 7/1991 | Summerton et al. ........ 538/391 |
| 5,142,047 A | 8/1992 | Summerton et al. |
| 5,166,315 A | 11/1992 | Summerton et al. ........ 528/406 |
| 5,185,444 A | 2/1993 | Summerton et al. |
| 5,194,428 A | 3/1993 | Agrawal et al. |
| 5,217,866 A | 6/1993 | Summerton et al. ........... 435/6 |
| 5,495,006 A | 2/1996 | Climie et al. |
| 5,506,337 A | 4/1996 | Summerton et al. ........ 528/391 |
| 5,521,063 A | 5/1996 | Summerton et al. ........... 435/6 |
| 5,576,302 A | 11/1996 | Cook et al. |
| 5,580,767 A | 12/1996 | Cowsert et al. |
| 5,698,685 A | 12/1997 | Summerton et al. ........ 536/24.3 |
| 5,702,891 A | 12/1997 | Kolberg et al. |
| 5,734,039 A | 3/1998 | Calabretta et al. |
| 5,738,985 A | 4/1998 | Miles et al. |
| 5,801,154 A | 9/1998 | Baracchini et al. |
| 5,892,023 A | 4/1999 | Pirotzky et al. |
| 5,955,318 A | 9/1999 | Simons et al. |
| 5,985,662 A | 11/1999 | Anderson et al. ........... 435/375 |
| 5,989,904 A | 11/1999 | Das et al. |
| 6,060,456 A | 5/2000 | Arnold et al. |
| 6,133,246 A | 10/2000 | McKay et al. |
| 6,174,868 B1 | 1/2001 | Anderson et al. |
| 6,214,555 B1 | 4/2001 | Leushner et al. |
| 6,228,579 B1 | 5/2001 | Zyskind et al. |
| 6,239,265 B1 | 5/2001 | Cook |
| 6,258,570 B1 | 7/2001 | Glustein et al. |
| 6,306,993 B1 | 10/2001 | Rothbard et al. |
| 6,365,351 B1 | 4/2002 | Iversen |
| 6,365,577 B1 | 4/2002 | Iversen |
| 6,391,542 B1 | 5/2002 | Anderson et al. |
| 6,495,663 B1 | 12/2002 | Rothbard |
| 6,667,152 B2* | 12/2003 | Miles et al. ................... 435/5 |
| 6,669,951 B2* | 12/2003 | Rothbard et al. ............. 424/436 |
| 6,677,153 B2 | 1/2004 | Iversen |
| 6,784,291 B2 | 8/2004 | Iversen et al. |
| 6,828,105 B2 | 12/2004 | Stein et al. |
| 6,841,542 B2 | 1/2005 | Bartelmez et al. |
| 6,841,675 B1* | 1/2005 | Schmidt et al. ............. 544/336 |
| 6,881,825 B1 | 4/2005 | Robbins et al. |
| 7,049,431 B2 | 5/2006 | Iversen et al. |
| 7,094,765 B1 | 8/2006 | Iversen et al. |
| 7,115,374 B2 | 10/2006 | Linnen et al. |
| 7,507,196 B2 | 3/2009 | Stein et al. |
| 7,524,829 B2 | 4/2009 | Stein et al. |
| 2003/0166588 A1 | 9/2003 | Iversen et al. |
| 2003/0171311 A1 | 9/2003 | Blatt et al. |
| 2003/0171335 A1 | 9/2003 | Stein et al. |
| 2003/0224353 A1 | 12/2003 | Stein et al. |
| 2004/0072239 A1 | 4/2004 | Renaud et al. |
| 2004/0259108 A1 | 12/2004 | Linnen et al. |

(Continued)

FOREIGN PATENT DOCUMENTS

| | | |
|---|---|---|
| WO | WO 98/12312 A1 | 3/1998 |
| WO | WO 0017391 A1 * | 3/2000 |
| WO | WO 02/26968 A2 | 4/2002 |
| WO | WO02/068637 A2 | 9/2002 |
| WO | WO03033657 A2 | 4/2003 |

(Continued)

OTHER PUBLICATIONS

Yuan et al., A phosphorothioate antisense oligodeoxynucleotide specifically inhibits coxsackievirus B3 replication in cardiomyocytes and mouse hearts, Published online Apr. 19, 2004, Laboratory Investigation, vol. 84, pp. 703-714.*

(Continued)

*Primary Examiner* — Dana Shin
(74) *Attorney, Agent, or Firm* — Seed IP Law Group PLLC

(57) ABSTRACT

The invention provides antisense antiviral compounds and methods of their use and production in inhibition of growth of viruses of the Picornaviridae family and in the treatment of a viral infection. The compounds are particularly useful in the treatment of *Enterovirus* and/or *Rhinovirus* infection in a mammal. The antisense antiviral compounds are substantially uncharged, including partially positively charged, morpholino oligonucleotides have a sequence of 12-40 subunits, including at least 12 subunits having a targeting sequence that is complementary to a region associated with viral RNA sequences within a 32 nucleotide region of the viral 5' untranslated region identified by SEQ ID NO:4.

10 Claims, 13 Drawing Sheets

U.S. PATENT DOCUMENTS

| | | | |
|---|---|---|---|
| 2004/0265879 | A1 | 12/2004 | Iversen et al. |
| 2005/0176661 | A1 | 8/2005 | Vaillant et al. |
| 2006/0063150 | A1 | 3/2006 | Iversen et al. |
| 2006/0148747 | A1 | 7/2006 | Stein et al. |
| 2006/0149046 | A1 | 7/2006 | Arar |
| 2006/0269911 | A1 | 11/2006 | Iversen et al. |
| 2007/0004661 | A1 | 1/2007 | Stein et al. |
| 2007/0066556 | A1 | 3/2007 | Stein et al. |
| 2008/0311556 | A1 | 12/2008 | Iversen et al. |

FOREIGN PATENT DOCUMENTS

| | | |
|---|---|---|
| WO | WO 2004097040 A1 * | 11/2004 |
| WO | WO 2005/007805 A2 | 1/2005 |
| WO | WO 2005/013905 A2 | 2/2005 |
| WO | WO 2005/030800 A2 | 4/2005 |
| WO | 2006/033933 | 3/2006 |
| WO | WO 2006/047683 A2 | 4/2006 |
| WO | 2007/030576 | 3/2007 |
| WO | 2007/030691 | 3/2007 |

OTHER PUBLICATIONS

Liu et al., Structural and functional analysis of the 5' untranslated region of coxsavkievirus B3 RNA: In vivo translational and infectivity studies of full-length mutants, 1999, Virology, vol. 265, pp. 206-217.*

Padalko et al., The interferon inducer Ampligen [Poly(I)-Poly(C12U)] markedly protects mice against Coxsackie B3 virus-induced myocarditis, 2004, Antimicrobial Agents and Chemotherapy, 2004, vol. 48, pp. 267-274.*

Moulton et al., 2003, Antisense and Nucleic Acid Drug Development, vol. 13, pp. 31-43.*

Agrawal et al. *Proc Natl Acad Sci U S A.*, 87(4):1401-5 (1990).

Bailey et al., "Cationic oligonucleotides can mediate specific inhibition of gene expression in *Xenopus* oocytes." *Nucleic Acids Res*, 26(21):4860-7 (1998).

Barawkar, D. A. and T. C. Bruise, "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci U S A*, 95(19): 11047-52. (1998).

Blommers et al., *Nucleic Acids Res.*, 22(20):4187-94 (1994).

Bonham et al., *Nucleic Acids Res.*, 23(7):1197-203 (1995).

Boudvillain et al., *Biochemistry* 36(10):2925-31 (1997).

Branch, Andrea D., *TIBS*, 23:45-50 (1998).

Brasey et al., *J. Virol.*, 77(7):3939-3949 (2003).

Cross et al., "Solution structure of an RNA x DNA hybrid duplex containing a 3'—thioformacetal linker and an RNA A-tract." *Biochemistry*, 36(14): 4096-107 (1997).

Dagle et al., "Targeted elimination of zygotic messages in *Xenopus laevis* embryos by modified oligonucleotides possessing terminal cationic linkages", *Nucleic Acids Res.*, 28(10): 2153-7 (2000).

Ding, D., et al., *Nucleic Acids Res* 24(2):354-60, (1996).

Egholm et al., "PNA hybridizes to complementary oligonucleotides obeying the Watson-Crick hydrogen-bonding rules." *Nature*, 365(6446): 566-8 (1993).

Felgner et al., *PNAS*, 84(21): 7413-7 (1987).

Gait et al., *J. Chem. Soc.*, 0(14):1684-1686 (1974).

Gee et al., *Antisense Nucleic Acid Drug Dev* 8(2):103-11 (1998).

Johannes at al., *PNAS*, 96(23):13118-23 (1999).

Lesnikowski et al., "Octa(thymidine methanephosphonates) of partially defined stereochemistry: synthesis and effect of chirality at phosphorus on binding to pentadecadeoxyriboadenylic acid." *Nucleic Acids Res.*, 18(8): 2109-15 (1990).

Linkletter, B. A. and Bruice, T.C., "Solid-phase synthesis of positively charged deoxynucleic guanidine (DNG) modified oligonucleotides containing neutral urea linkages: Effect of charge deletions on binding and fidelity." *Bioorg. Med. Chem.* 8(11): 1893-1901 (2000).

Micklefield, J., "Backbone modification of nucleic acids: synthesis, structure and therapeutic applications." *Curr Med Chem*, 8(10):1157-79 (2001).

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem.*, 12(1): 154-7.

Moulton, H. M., M. H. Nelson, et al., *Bioconjug Chem* 15(2):290-9 (2004).

Nelson et al., "Arginine-rich peptide conjugation to morpholino oligomers: effects on antisense activity and specificity." *Bioconjug Chem.*, 16(4): 959-66 (2005).

Stein, D., et al., *Antisense Nucleic Acid Drug Dev* 7(3):151-7, (1997).

Summerton et al., *Antisense & Nucleic Acid Drug Development*, 7:63-70 (1997).

Summerton et al., *Biochim et. Biophys. ACTA*, 1489:141-158 (1999).

Summerton, J. and D. Weller, "Morpholino antisense oligomers: design, preparation, and properties.", *Antisense Nucleic Acid Drug Dev.*, 7(3): 187-95 (1997).

Toulme et al., Targeting RNA structures by antisense oligonucleotides. *Biochimie*, 78(7): 663-73 (1996).

Wilson et al., *Mol. Cell Biol.*, 20(14):4990-4999 (2000).

U.S. Appl. No. 11/431,968, filed May 10, 2006, Stein et al.

Banerjee, R. and A. Dasgupta "Interaction of picornavirus 2C polypeptide with the viral negative-strand RNA." *J Gen Virol*, 82(Pt 11):2621-7 (2001).

Banerjee, R. and A. Dasgupta, "Specific interaction of hepatitis C virus protease/helicase NS3 with the 3'-terminal sequences of viral positive- and negative-strand RNA." J Virol 75(4):1708-21 (2001).

Banerjee, R., A. Echeverri, et al., "Poliovirus-encoded 2C polypeptide specifically binds to the 3'-terminal sequences of viral negative-strand RNA." J Virol 71(12):9570-8 (1997).

Banerjee, R., W. Tsai, et al., "Interaction of poliovirus-encoded 2C/2BC polypeptides with the 3' terminus negative-strand cloverleaf requires an intact stem-loop b." *Virology*, 280(1): 41-51 (2001).

Barawkar, D. A. and T. C. Bruice, "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci U S A*, 95(19):11047-52 (1998).

Clarke et al., *J. Infect. Diseases*, 181:S309-S316 (2000).

Corey et al., Morpgolino Antisnese Oligonucleotides: Tools for Investigating Vertebrate Development, *Genome Biology*, 2(5):1015.1-1015.3 (2001).

Freier, S.M., in Antisense Drug Technology: Principles, Strategies, and Applications, Ch. 5, pp. 107-118, (2001).

Green et al., *J. Am. Coll. Surg.*, 191:93-105 (2000).

Hanecak et al., *Journal of Virology*, 70(8):5203-5212 (1996).

Holland et al., Emerging Virus, Morse, S.S., Ed., Oxford University Press, New York and Oxford pp. 203-218 (1993).

Jaeger, J.A., et al., Proc. Natl. Acad. Sci. USA 86:7706-7710, (1989).

Lopez De Quinto S. et al., *Virology*, 255(2):324-336 (1999).

Markoff, L., *Adv. Virus Res.*, 59:177-228 (2003).

Moulton et al., Abstracts of Papers American Chemical Society National Meeting 226 (1-2): Biol 75 (Sep. 7-11, 2003).

National Center for Biotechnology Information Report No. AF029248 from NCBI Genome Database (2000).

National Center for Biotechnology Information Report No. NC_002645 from NCBI Genome Database (2001).

National Center for Biotechnology Information Report No. AY274119 from NCBI Genome Database (2003).

Neuman, B.W., et al., *Journal of Virology* 78(11):5891-5899 (2004).

O'Ryan et al., in: *Spector S, Lancz G*, Eds., Clinical Virology Manual, New York, Elsevier Science pp. 361-396 (1992).

Orr et al., *Current Opinion in Molecular Therapeuctics, Current Drugs*, 2(3):325-331 (2000).

Pardigon, N. and J. H. Strauss, "Cellular proteins bind to the 3' end of Sindbis virus minus-strand RNA." *J Virol.*, 66(2):1007-15 (1992).

Pardigon, N., E. Lenches, et al., "Multiple binding sites for cellular proteins in the 3' end of *Sindbis alphavirus* minus-sense RNA." *J Virol.*, 67(8):5003-11 (1993).

Partridge et al., Antisense Nucleic Acid Drug Development, 6(3):169-175 (1996).

Paul, A. V. (2002). Possible unifying mechanism of picornavirus genome replication. *Molecular Biology of Picornaviruses*. B. L. Semler and E. Wimmer. Washington, DC, ASM Press:227-246.

Roehl, H. H. and B. L. Semler, "Poliovirus infection enhances the formation of two ribonucleoprotein complexes at the 3' end of viral negative-strand RNA." *J Virol.*, 69(5):2954-61 (1995).

Roehl, H. H., T. B. Parsley, et al., "Processing of a cellular polypeptide by 3CD proteinase is required for poliovirus ribonucleoprotein complex formation." *J Virol.* 71(1):578-85 (1997).

Rothbard et al., *J. Med. Chem.*, 45:3612-3618 (2002).

Sankar e al., *European Journal of Biochemistry*, 184(1):39-45 (1989).

Siprashvili, Z., et al., *Human Gene Therapy*, 14:1225-1233 (2003).

Smith et al., *Emerg. Inf. Dis.*, 4:13-20 (1998).

Smith, R.M. and Wu, G.Y., *Journal of Viral Hepatitis*, 11:115-123 (2004).

Stein et al., *Antisense Nucleic Acid Drug Development*, 11(5):317-325 (2001).

Thiel et al., *Journal of General Virology*, 82:1273-1281 (2001).

Wages et al., *Biotechniques*, 23:1116-1121 (1997).

Wang et al., *Antimicrobial Agents Chemotherapy*, 45(4):1043-1052 (2001).

Wei et al., *Nucleic Acids Res.*, 28:3065-3074 (2000).

Wu et al., *J. Biol. Chem.*, 267:12436-12439 (1992).

Xu et al., *Revue Scientifique Technique*, Office of International des Epizooties 10:2393-2408 (1991).

Xu, W. Y. (1991). "Viral haemorrhagic disease of rabbits in the People's Republic of China: epidemiology and virus characterisation." *Rev Sci Tech*, 10(2):393-408.

Zhang et al., *Antimicrobial Agents Chemotherapy*, 43(2):347-353 (1999).

Zuker, M., *Nucleic Acids Res.*, 31(13):3406-3415 (2003).

Peter M. Fischer, Cellular Uptake Mechanisms and Potential Therapeutic Utility of Peptidic Cell Delivery Vectors: Progress 2001-2006, Published online 2006 Wiley Interscience, pp. 1-41.

McCaffrey et al., *Hepatology*, 38:503-508 (Aug. 2003).

Agrawal et al. "Oligodeoxynucleoside phosphoramidates and phosphorothioates as inhibitors of human immunodeficiency virus", *Proc Natl Acad Sci USA.*, 85(19):7079-7083 (1988).

Agrawal et al., "Antisense Therapeutics: Is it as Simple as Complementary Base Recognition?", *Molecular Medicine Today*, 6:72-81 (2000).

Arora and Iversen, "Redirection of drug metabolism using antisense technology", *Curr. Opin Mol. Ther.*, 3(3):249-257 (2001).

Bailey, C. P., J. M. Dagle et al., "Cationic oligonucleotides can mediate specific inhibition of gene expression in *Xenopus* oocytes." *Nucleic Acids Res*, 26(21): 4860-7 (1998).

Basler et al., "The Ebola virus VP35 protein functions as a type I IFN antagonist", *Proc. Natl. Acad. Sci. U.S.A.*,97(22):12289-12294 (2000).

Borio, L. et al., "Hemorrhagic fever viruses as biological weapons: medical and public health management", *The Journal of the American Medical Association*, 287(18):2391-2405 (2002).

Bray, M. et al., "A mouse model for evaluation of prophylaxis and therapy of Ebola hemorrhagic fever",*The Journal of Infectious Diseases*, 178(3):651-661 (1998).

Burnett, J.C. et al., "The evolving field of biodefence: therapeutic developments and diagnostics", *Natural Review Drug Discovery*, 4:281-297 (2005).

Callahan, P.L. et al. "Molecular cloning and complete sequence determination of RNA genome of human rhinovirus type 14", *Proc. Natl. Acad. Sci. U.S.A.*, 82(3):732-736 (1985).

Chirilla et al., "The use of synthetic polymers for delivery of therapeutic antisense oligodeoxynucleotides", *Biomaterials*, 23(2):321-342 (2002).

Connolly, B.M. et al., "Pathogenesis of experimental Ebola virus infection in guinea pigs", *The Journal of Infectious Diseases*, 179(Suppl. 1):S203-S217 (1999).

Cox, N. J. and Subbaro, K., "Global Epidemiology of Influenza: Past and Present", *Annual review Medicine*, 51:407-421 (2000).

Cox, N. J. and Subbaro, K., "Influenza", *Lancet*, 354(9186):1277-1282 (1999).

Crooke, R.M. et al. "In vitro toxicological evaluation of ISIS 1082, a phosphorothioate oligonucleotide inhibitor of herpes simplex virus", *Antimicrobial Agents and Chemotherapy*, 36(3):527-532 (1992).

Crooke, S. T., Antisense Drug Technology: Principles, Strategies, and Applications. New York, Marcel Dekker, S. Crooke Ed Springer pp. 1-50 (1999).

Deas, T.S., et al., "Inhibition of flavivirus infections by antisense oligomers specifically suppressing viral translation and RNA replication", *Journal of Virology*, 79(8):4599-4609, (2005).

Faria, M. et al., "Phosphoramidate oligonucleotides as potent antisense molecules in cells and in vivo", *Nature Biotechnology*, 19(1):40-44 (2001).

Feldman, H. et al., "Molecular Biology and Evolution of Filoviruses", *Arch. Virol.*, 7(Suppl.):81-100 (1993).

Feldman, H. et al., *Current Topics in Microbiology and Immunology*, Classsification, Structure, and Replication of Filoviruses, pp. 1-21 (1999).

Feldmann, H. et al., "Ebola Virus: from Discovery to Vaccine", *Nature Review Immunology*, 3(8):677-685 (2003).

Geisbert, T.W. and Hensley, L.E.,"Ebola virus: new insights into disease aetiopathology and possible therapeutic interventions", *Expert Reviews in Molecular Medicine*, 6(20):1-24 (2004).

Geisbert, T.W. et al.,"Treatment of Ebola virus infection with a recombinant inhibitor of factor VIIa/tissue factor: a study in rhesus monkeys", *The Lancet*, 362(9400):1953-1958 (2003).

Genbank Accession No. AF304460, Human coronavirus 229E, complete genome (Jul. 2001).

Gilbert et al., "Sieve analysis: methods for assessing from vaccine trial data how vaccine efficacy varies with genotypic and phenotypic pathogen variation", *Journal of Clinical Epidemiology*, 54(1):68-85 (2001).

Hudziak et al., "Resistance of morpholino phosphorodiamidate oligomers to enzymatic degradation", *Antisnese & Nucleic Acid Drug Developement.*, 6:267-272 (1996).

Jahrling, P.B. et al., "Evaluation of immune globulin and recombinant interferon-alpha2b for treatment of experimental Ebola virus infections", *The Journal of Infectious Diseases*, 179(Suppl 1):S224-S234 (1999).

Jen et al., "Suppression of Gene Expression by Targeted Disruption of Messenger RNA:Available Options and Current Strategies", *Stem Cells*, 18:307-319 (2000).

Jubin, R., et al., "Hepatitis C virus internal ribosome entry site (IRES) stem loop llld contains a phylogenetically conserved GGG triplet essential for translation and IRES folding", *Journal of Virology*, 74(22):10430-10437 (2000).

Kinney, et al., "Inhibition of Denguie Virus Serotypes 1 to 4 in Vero cell cultures with Morpholino Oligomers", *Journal of Virology*, 79:5116-5128 (2005).

Lee, W-M. et al., "Complete sequence of the RNA genome of human rhinovirus 16, a clinically useful common cold virus belonging to the ICAM-1 receptor group", *Virus Genes*, 9(2):177-184 (1994).

Miranda, M.B. et al., "Differential activation of apoptosis regulatory pathways during monocytic vs granulocytic differentiation: a requirement for Bcl-X(L)and XIAP in the prolonged survival of monocytic cells", *Journal of the Leukemia Society of America*, 17(2):1157-79 (2001).

Mizuta, T. et al., "Antisense oligonucleotides directed against the viral RNA polymerase gene enhance survival of mice infected with influenza A", *Nature Biotechnology*, 17(6):583-587 (1999).

NCBI Genbank Nucleotide Accession No. AF091736, VESV-like calicivirus strain Pan-1, complete genome, 5 pages (1998).

NCBI Genbank Nucleotide Accession No. AF169005, Hepatitis C virus subtype 2a isolate NDM59, complete genome, 5 pages (1999).

Palu et al., "In pursuit of new developments for gene therapy of human diseases", *Journal of Biotechnology*, 68:1-13 (1999).

Peters, C.J. and Ledue, J.W., "An introduction to Ebola: the virus and the disease", *The Journal of Infectious Diseases*, 179(Suppl 1):ix-xvi (1999).

Raviprakash, K., et al., "Inhibition of dengue virus by novel, modified antisense oligonucleotides", *Journal of Virology*, 69(1):69-74, (1995).

Robaczewska, M. et al., "Inhibition of hepadnaviral replication by polyethylenimine-based intravenous delivery of antisense phosphodiester oligodeoxynucleotides to the liver.", *Gene Therapy*, 8:874-881 (2001).

Sanchez, A. et al., "Sequence analysis of the Ebola virus genome: organization, genetic elements, and comparison with the genome of Marburg virus", *Virus Research*, 29(3):215-240 (1993).

Scanlon, K.I, "Anti-genes: siRNA, ribozymes and antisense", *Current Pharmaceutical Biotechnology*, 5(5):415-420 (2004).

Shabbits, J.A. et al., "Tumor chemosensitization strategies based on apoptosis manipulations", *Molecular Cancer Therapeuctics*, 2(8):805-813 (2003).

Shengqi et al., "Synthesis of Antisense Phosphothioate Oligodeoxynucleotides of Dengue Fever Virus and Their Anti-Viral Activity", *Progress in Biochemistry and Biophsics*, 24:64-68 (English Translation) (1997).

Smith et al., "Antisense treatment of caliciviridae: an emerging disease agent of animals and humans", *Current Opinion Molecular Therapeutcis*, 4(2):177-184.

Sosnovtsev, S. and Green K.Y, "RNA transcripts derived from a cloned full-length feline calicivirus genome do not require VpG for infectivity", *Virology*, 210:383-390 (1995).

Taylor et al., "Antisense oligonucleotides: a systematic high-throughput approach to target validation and gene function determination", *Drug Discovery Today*, 4:562-567 (1999).

Vlasov et al., "Inhibition of the Influenza Virus M Protein mRNA Transaltion in vitro with Complementary Oligonucleotides", *Nucleosides & Nucleotides*, 10(13):649-650 (1991).

Warfield, K.I. et al., "Role of natural killer cells in innate protection against lethal ebola virus infection", *The Journal of Experimental Medicine*, 200(2):169-179 (2004).

Williams, A.S. et al., "A single intra-articular injection of liposomally conjugated methotrexate suppresses joint inflammation in rat antigen-induced arthritis", *British Journal of Rheumatology*, 35(8):719-724 (1996).

Wu, G.Y. and Wu, C.H., "Receptor-mediated in vitro gene transformation by a soluble DNA carrier system", *J. Biol. Chem.* 262(10):4429-4432 (1987).

Zollinger, W.D. and Moran, E., "Meningococcal vaccines—present and future", *Transactions of Royal Soc of Tropical Medicine and Hygiene*, 85(Supp. 1):37-43 (1991).

Anderson et al., "Inhibition of Human Cytomegalovirus Immediate-Early Gene Expression by an Antisense Oligonucleotide Complementary to Immediate-Early RNA" Antimicrobial Agents and Chemotherapy 40(9):2004-2011, 1996.

Corver et al., "Fine Mapping of a *cis*-Acting Sequence Element in Yellow Fever Virus RNA That Is Required for RNA Replication and Cyclization" Journal of Virology 77(3):2265-2270, 2003.

"Enterovirus Surveillance—United States, 2000-2001" MMWR Weekly 51(46):1047-1049, 2002.

Hahn et al., "Conserved Elements in the 3' Untranslated Region of Flavivirus RNAs and Potential Cyclization Sequences" J. Mol. Biol. 198:33-41, 1987.

International Search Report, for Application No. PCT/US2004/025401, mailed Apr. 27, 2005, 3 pages.

International Search Report, for Application No. PCT/US2005/032815, mailed May 5, 2006, 6 pages.

International Search Report, for Application No. PCT/US2006/034786, mailed Apr. 24, 2007, 2 pages.

International Search Report, for Application No. PCT/US2006/034986, mailed Apr. 24, 2007, 2 pages.

Khromykh et al., "Essential Role of Cyclization Sequences in Flavivirus RNA Replication" Journal of Virology 75(14):6719-6728, 2001.

Stone et al., "A Morpholino Oligomer Targeting Highly Conserved Internal Ribosome Entry Site Sequence Is Able to Inhibit Multiple Species of Picornavirus" Antimicrobial Agents and Chemotherapy 52(6):1970-1981, 2008.

You et al., "In Vitro RNA Synthesis from Exogenous Dengue Viral RNA Templates Requires Long Range Interactions between 5'- and 3'- Terminal Regions That Influence RNA Structure" The Journal of Biological Chemistry 276(19):15581-15591, 2001.

Liu et al., "Antisense oligonucleotide inhibition of coxsackievirus B2 gene in HeLa cells and dose-response experiments," *Chinese J. Exp. Clin. Virol.* 18(1), Mar. 2004, 1 page, (Abstract).

Martinand-Mari et al., "Oligonucleotide-based Strategies to Inhibit Human Hepatitis C Virus," *Oligonucleotides* 13:539-548, 2003.

Nulf et al., "Intracellular inhibition of hepatitis C virus (HCV) internal ribosomal entry site (IRES)-dependent translation by peptide nucleic acids (PNAs) and locked nucleic acids (LNAs)," *Nucleic Acids Research* 32(13):3792-3798, 2004.

\* cited by examiner

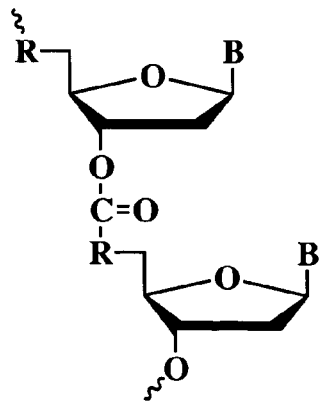
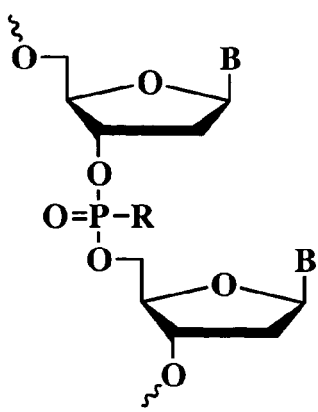
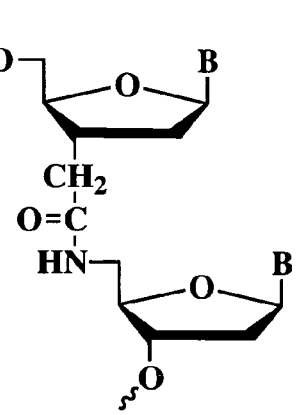
Fig. 2A          Fig. 2B          Fig. 2C
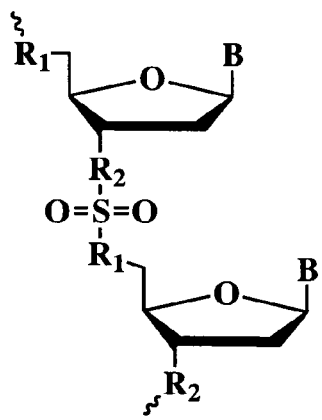
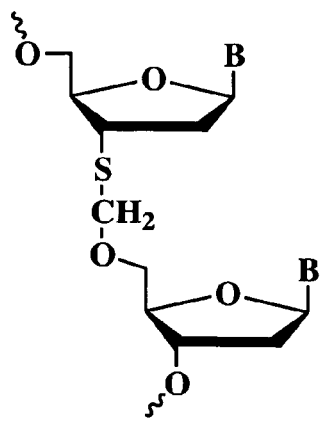
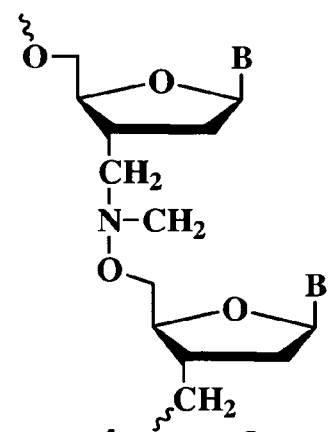
Fig. 2D          Fig. 2E          Fig. 2F
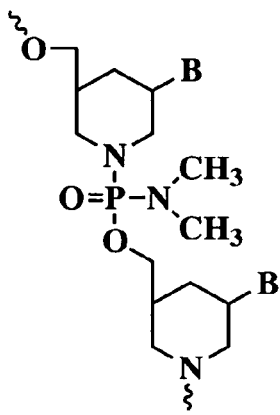
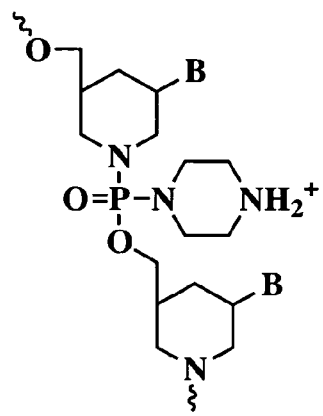
Fig. 2G          Fig. 2H

```
              **   ***  *********************
           1  GCGGAACCGACTACTTTGGGTGTCCGTGTTTC
SEQ ID NOS: 3 ACGGGACCGACTACTTTGGGTGTCCGTGTTTC
           2  ATGGGACCAACTACTTTGGGTGTCCGTGTTTC
           4  RYGGRACCRACTACTTTGGGTGTCCGTGTTTC
              ←────── 3'-32 Target Region ──────→
```

Fig. 3

SEQUENCE LISTING

<160> NUMBER OF SEQ ID NOS: 20

<210> SEQ ID NO 1
<211> LENGTH: 32
<212> TYPE: DNA
<213> ORGANISM: Artificial Sequence
<220> FEATURE:
<223> OTHER INFORMATION: Target Sequence based on Picornavirus Sequence

<400> SEQUENCE: 1
gcggaaccga ctactttggg tgtccgtgtt tc                32

<210> SEQ ID NO 2
<211> LENGTH: 32
<212> TYPE: DNA
<213> ORGANISM: Artificial Sequence
<220> FEATURE:
<223> OTHER INFORMATION: Target Sequence based on Picornavirus Sequence

<400> SEQUENCE: 2
atgggaccaa ctactttggg tgtccgtgtt tc                32

-continued

```
<210> SEQ ID NO 3
<211> LENGTH: 32
<212> TYPE: DNA
<213> ORGANISM: Artificial Sequence
<220> FEATURE:
<223> OTHER INFORMATION: Target Sequence based on Picornavirus Sequence

<400> SEQUENCE: 3
acgggaccga ctactttggg tgtccgtgtt tc                                    32

<210> SEQ ID NO 4
<211> LENGTH: 32
<212> TYPE: DNA
<213> ORGANISM: Artificial Sequence
<220> FEATURE:
<223> OTHER INFORMATION: Target Sequence based on Picornavirus Sequence

<400> SEQUENCE: 4
ryggraccra ctactttggg tgtccgtgtt tc                                    32

<210> SEQ ID NO 5
<211> LENGTH: 32
<212> TYPE: DNA
<213> ORGANISM: Artificial Sequence
<220> FEATURE:
<223> OTHER INFORMATION: Synthetic Oligomers

<400> SEQUENCE: 5
gaaacacgga cacccaaagt agtcggttcc gc                                    32

<210> SEQ ID NO 6
<211> LENGTH: 37
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)...(37)
<223> OTHER INFORMATION: n = A,T,C or G

<400> SEQUENCE: 6
aaaangaaac acggacaccc aaagtagtcg gttccgc                               37

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 7
cacccaaagt agtcggttcc                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 8
cacggacacc caaagtagtc                                                  20

<210> SEQ ID NO 9
<211> LENGTH: 20
<212> TYPE: DNA
<213> ORGANISM: Artificial Sequence
```

```
<220> FEATURE:
<223> OTHER INFORMATION: Synthetic Oligomer

<400> SEQUENCE: 9
ggaaacacgg acacccaaag                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 10
aaaaggaaac acggacaccc                                               20

<210> SEQ ID NO 11
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 11
atgaaacacg gacacccaaa g                                             21

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 12
gaaacacgga cacccaaagt ag                                            22

<210> SEQ ID NO 13
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 13
gagaaacacg gacacccaaa gtag                                          24

<210> SEQ ID NO 14
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 14
taagcagcca gtataggaat a                                             21

<210> SEQ ID NO 15
<211> LENGTH: 13
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (12)..(12)
<223> OTHER INFORMATION: Xaa is 6-aminohexanoic acid
```

```
<220> FEATURE:
<221> NAME/KEY: MOD_RES
<222> LOCATION: (13)..(13)
<223> OTHER INFORMATION: Xaa is beta-alanine

<400> SEQUENCE: 15

Arg Arg Arg Arg Arg Arg Arg Arg Arg Phe Phe Xaa Xaa
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(13)
<223> OTHER INFORMATION: Xaa is 6-aminohexanoic acid
<220> FEATURE:
<221> NAME/KEY: MOD_RES
<222> LOCATION: (14)..(14)
<223> OTHER INFORMATION: Xaa is beta-alanine

<400> SEQUENCE: 16

Arg Xaa Arg Arg Xaa Arg Arg Xaa Arg Arg Xaa Arg Xaa Xaa
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(16)
<223> OTHER INFORMATION: Xaa is 6-aminohexanoic acid
<220> FEATURE:
<221> NAME/KEY: MOD_RES
<222> LOCATION: (17)..(17)
<223> OTHER INFORMATION: Xaa is beta-alanine

<400> SEQUENCE: 17

Arg Xaa Arg Xaa Arg Xaa Arg Xaa Arg Xaa Arg Xaa Arg Xaa Arg Xaa Xaa
1               5                   10                  15

<210> SEQ ID NO 18
<211> LENGTH: 9
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(8)
<223> OTHER INFORMATION: Xaa is 6-aminohexanoic acid
<220> FEATURE:
<221> NAME/KEY: MOD_RES
<222> LOCATION: (9)..(9)
<223> OTHER INFORMATION: Xaa is beta-alanine

<400> SEQUENCE: 18

Arg Xaa Arg Xaa Arg Xaa Arg Xaa Xaa
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic arginine-rich peptide
```

-continued

<220> FEATURE:
<221> NAME/KEY: MOD_RES
<222> LOCATION: (2)..(7)
<223> OTHER INFORMATION: Xaa is 6-aminohexanoic acid
<220> FEATURE:
<221> NAME/KEY: MOD_RES
<222> LOCATION: (8)..(8)
<223> OTHER INFORMATION: Xaa is beta-alanine

<400> SEQUENCE: 19

Arg Xaa Arg Arg Xaa Arg Xaa Xaa
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2)..(10)
<223> OTHER INFORMATION: Xaa is 6-aminohexanoic acid
<220> FEATURE:
<221> NAME/KEY: MOD_RES
<222> LOCATION: (11)..(11)
<223> OTHER INFORMATION: Xaa is beta-alanine

<400> SEQUENCE: 20

Arg Xaa Arg Arg Xaa Arg Arg Xaa Arg Xaa Xaa
1               5                   10

ANTISENSE ANTIVIRAL COMPOUND AND METHOD FOR TREATING PICORNAVIRUS INFECTION

CROSS-REFERENCE TO RELATED APPLICATIONS

This application claims the benefit of U.S. Provisional Application No. 60/715,888, filed Sep. 8, 2005 and U.S. Provisional Application No. 60/800,120, filed May 11, 2006, both incorporated herein by reference in their entirety.

FIELD OF THE INVENTION

This invention relates to antisense oligonucleotide compounds for use in treating a picornavirus infection and antiviral treatment methods employing the compounds.

REFERENCES

Agrawal, S., S. H. Mayrand, et al. (1990). *Proc Natl Acad Sci USA* 87(4): 1401-5.
Blommers, M. J., U. Pieles, et al. (1994). *Nucleic Acids Res* 22(20): 4187-94.
Bonham, M. A., S. Brown, et al. (1995). *Nucleic Acids Res* 23(7): 1197-203.
Boudvillain, M., M. Guerin, et al. (1997). *Biochemistry* 36(10): 2925-31.
Brasey, A., M. Lopez-Lastra, et al. (2003). *J Virol* 77(7): 3939-49.
Cross, C. W., J. S. Rice, et al. (1997). *Biochemistry* 36(14): 4096-107.
Dagle, J. M., J. L. Littig, et al. (2000). *Nucleic Acids Res* 28(10): 2153-7.
Ding, D., S. M. Grayaznov, et al. (1996). *Nucleic Acids Res* 24(2): 354-60.
Egholm, M., O. Buchardt, et al. (1993). *Nature* 365(6446): 566-8.
Felgner, P. L., T. R. Gadek, et al. (1987). *Proc Natl Acad Sci USA* 84(21):7413-7.
Gait, M. J., A. S. Jones, et al. (1974). *J Chem Soc [Perkin 1]* 0(14): 1684-6.
Gee, J. E., I. Robbins, et al. (1998). *Antisense Nucleic Acid Drug Dev* 8(2):103-11.
Johannes, G., M. S. Carter, et al. (1999). *Proc Natl Acad Sci USA* 96(23):13118-23.
Lesnikowski, Z. J., M. Jaworska, et al. (1990). *Nucleic Acids Res* 18(8):2109-15.
Mertes, M. P. and E. A. Coats (1969). *J Med Chem* 12(1): 154-7.
Moulton, H. M., M. H. Nelson, et al. (2004). *Bioconjug Chem* 15(2): 290-9.
Nelson, M. H., D. A. Stein, et al. (2005). *Bioconjug Chem* 16(4): 959-66.
Strauss, J. H. and E. G. Strauss (2002). *Viruses and Human Disease*. San Diego, Academic Press.
Summerton, J. and D. Weller (1997). *Antisense Nucleic Acid Drug Dev* 7(3):187-95.
Toulme, J. J., R. L. Tinevez, et al. (1996). *Biochimie* 78(7): 663-73.
Wilson, J. E., M. J. Powell, et al. (2000). *Mol Cell Biol* 20(14): 4990-9.

BACKGROUND OF THE INVENTION

The Picornaviridae represents a very large family of small RNA viruses responsible for many serious human and animal diseases (Strauss and Strauss 2002). The Picornaviridae include four major genera: *Enterovirus, Rhinovirus, Apthovirus* and *Hepatovirus*. The *Enterovirus* genus includes polioviruses, coxsackieviruses, echoviruses, and enteroviruses.

Poliovirus is the etiologic agent of the disease poliomyelitis in humans, and there are three known serotypes of the virus. The oral poliovaccine, typically given to children, is a mixture of the Sabin strain of the virus. The oral poliovirus vaccine is safe and effective, yet has two limitations. First, the vaccine is unstable since current vaccines are inactivated by relatively brief (less than 24 hours) exposure to temperatures of 37° C. This necessitates transport in a frozen state to the locale where they are administered. Second, the vaccine occasionally reverts to virulence in vaccine recipients and the reverted virulent virus may then be passed to other individuals who come into contact with the recipient in whom the vaccine has reverted.

The human rhinoviruses consist of at least 100 serotypes and are the primary causative agents of the common cold. Because of the large number of serotypes, development of a vaccine is problematic and antiviral agents may therefore be the best approach to treatment. The Coxsackie viruses and other human enteroviruses (multiple serotypes), are associated with a wide range of human diseases including summer flus, diarrhea, meningitis, hepatitis, pneumonia, myocarditis, pericarditis, and diabetes. These infections occur sporadically in the general population, but are becoming more common among children in day care and their parents and siblings. Other important members of the Picornaviridae family include human hepatitis A virus, Theiler's murine encephalomyelitis virus, foot-and-mouth disease virus, and mengovirus.

The existing drugs which are used against the viruses described above are only moderately effective, and are typically effective against only a limited subset of the rhinovirus serotypes. In general, the available drugs have either failed to demonstrate sufficient prophylactic effects or are converted in the body into inactive metabolites.

Thus, there remains a need for a more effective antiviral therapy in several members of the Picornoviridae family.

SUMMARY OF THE INVENTION

The invention includes, in one aspect, a method of inhibiting viral infection in mammalian cells by an *Enterovirus* or *Rhinovirus* in the Picornaviridae family. The method includes the steps of exposing the cells to an antisense oligonucleotide compound, thereby to form a heteroduplex structure (i) composed of the virus' positive sense strand and the oligonucleotide compound, and (ii) characterized by a Tm of dissociation of at least 45° C. The oligonucleotide compound is characterized by:

(i) a substantially uncharged, nuclease-resistant backbone,
(ii) capable of uptake by mammalian host cells,
(iii) containing between 12-40 nucleotide bases, and
(iv) having a targeting sequence of at least 12 subunits complementary to SEQ ID NO:4 in the positive-sense strand of the virus.

The compound to which the host cells are exposed may be composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages having the structure:

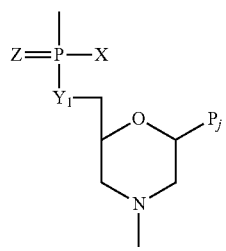

where $Y_1=O$, $Z=O$, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino, e.g., wherein $X=NR_2$, where each R is independently hydrogen or methyl.

The compound may be composed of morpholino subunits linked with the uncharged linkages described above interspersed with linkages that are positively charged at physiological pH. The total number of positively charged linkages is between 2 and no more than half of the total number of linkages. The positively charged linkages have the structure above, where X is 1-piperazine.

The oligonucleotide compound to which the cells are exposed may have a sequence contained in SEQ ID NO:6, such as one of the sequences identified by SEQ ID NOS:7-13. The compound may be conjugated to an arginine-rich polypeptide effective to promote uptake of the compound into infected host cells. Exemplary polypeptides have one of the sequences identified as SEQ ID NOS:15-20.

For use in treating a mammalian subject infected by an *Enterovirus* or *Rhinovirus* in the Picornaviridae family, the compound is administered to the subject in a pharmaceutically effective amount. Compound administration may be continued until a significant reduction in viral infection or the symptoms thereof is observed. The subject may be treated with a second anti-viral compound before, after, or during treatment with the oligonucleotide compound.

For use in treating a mammalian subject at risk of infection by an *Enterovirus* or *Rhinovirus* in the Picornaviridae family, the compound is administered to the subject in an amount effective to inhibit infection of subject host cells by the virus.

In another aspect, the invention includes an oligonucleotide compound for use in inhibiting viral infection in mammalian cells by an *Enterovirus* or *Rhinovirus* in the Picornaviridae family. The compound is characterized by:

(i) a substantially uncharged, nuclease-resistant backbone, (ii) capable of uptake by mammalian host cells, (iii) containing between 12-40 nucleotide bases, (iv) having a targeting sequence of at least 12 subunits contained in SEQ ID NO:6; and (v) capable of binding to the virus' positive sense strand to form a heteroduplex structure having by a Tm of dissociation of at least 45° C.

The compound may be composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages having the structure:

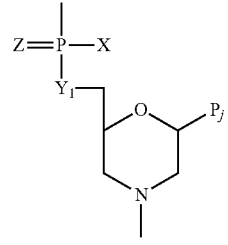

where $Y_1=O$, $Z=O$, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino, e.g., wherein $X=NR_2$, where each R is independently hydrogen or methyl.

The compound may be composed of morpholino subunits linked with the uncharged linkages described above interspersed with linkages that are positively charged at physiological pH. The total number of positively charged linkages is between 2 and no more than half of the total number of linkages. The positively charged linkages have the structure above, where X is 1-piperazine.

The oligonucleotide compound may have one of the sequences identified by SEQ ID NOS:7-13. The compound may be conjugated to an arginine-rich polypeptide effective to promote uptake of the compound into infected host cells. Exemplary polypeptides have one of the sequences identified as SEQ ID NOS:15-20.

The compound may be formulated in combination with another anti-viral compound.

These and other objects and features of the invention will become more fully apparent when the following detailed description of the invention is read in conjunction with the accompanying drawings.

BRIEF DESCRIPTION OF THE FIGURES

FIGS. 2A-2G show examples of uncharged linkage types in oligonucleotide analogs. FIG. 2H is an example of a preferred charged, cationic linkage.

FIG. 3 shows the sequence conservation across a broad spectrum of picornaviruses for the 3'-32 nct region represented by SEQ ID NOS:1-3, and the combined sequence identified by SEQ ID NO:4.

DETAILED DESCRIPTION OF THE INVENTION

I. Definitions

The terms below, as used herein, have the following meanings, unless indicated otherwise:

The term "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 50-100%, typically at least 80% of its linkages, are uncharged at physiological pH, and contain a single phosphorous atom. The analog contains between 8 and 40 subunits, typically about 8-25 subunits, and preferably about 12 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide analog" is an oligonucleotide analog composed of morpholino subunit structures of the form shown in FIGS. 1A-1D where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference in their entirety.

Figure 1A:
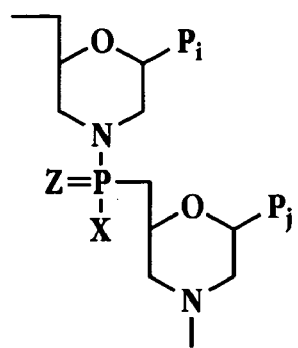
FIGS. 1A-1D show the repeating subunit segment of exemplary morpholino oligonucleotides, designated A through D.
Figure 1B:
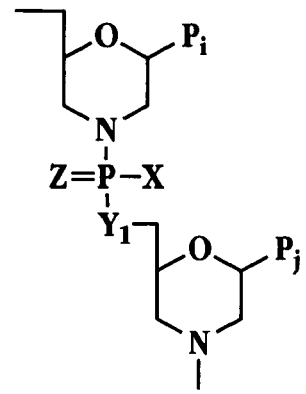

The subunit and linkage shown in FIG. 1B are used for six-atom repeating-unit backbones, as shown in FIG. 1B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_1$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures such as shown in FIG. 2B, where $X=NH_2$, NHR, or $NR_2$ (where R is lower alkyl, preferably methyl), $Y=O$, and $Z=O$, and Pi and Pj are purine or pyrimidine base-pairing moieties effective to bind, by base-specific hydrogen bonding, to a base in a polynucleotide, as seen in FIG. 2G. Also preferred are morpholino oligomers where the phosphordiamidate linkages are uncharged linkages as shown in FIG. 2G interspersed with cationic linkages as shown in FIG. 2H where, in FIG. 2B, X=1-piperazino. In another FIG. 2B embodiment, X=lower alkoxy, such as methoxy or ethoxy, Y=NH or NR, where R is lower alkyl, and Z=O.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "picornavirus" refers to one or more viral species belonging to the Picornaviridae family and specifically the *Enterovirus* and *Rhinovirus* genera of the Picornaviridae.

As used herein, the term "target" refers to a viral genomic RNA, and specifically, to a region identified by SEQ ID NO:4 within the 5'-untranslated region (5'-UTR) of the positive-sense RNA strand of a member of the Picornaviridae described herein.

The term "target sequence" refers to a portion of the target RNA against which the oligonucleotide analog is directed, that is, the sequence to which the oligonucleotide analog will hybridize by Watson-Crick base pairing of a complementary sequence. As will be seen, the target sequence may be a contiguous region of the viral positive-strand RNA, or may be composed of complementary fragments of both the 5' and 3' sequences involved in secondary structure.

The term "targeting sequence" is the sequence in the oligonucleotide analog that is complementary (meaning, in addition, substantially complementary) to the target sequence in the RNA genome. The entire sequence, or only a portion of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence. As will be seen, the target and targeting sequences are selected such that binding of the analog is to a region within; 1) the 5' untranslated region of the positive sense viral RNA and; 2) the internal ribosome entry site within the 5' untranslated region.

Target and targeting sequences are described as "complementary" to one another when hybridization occurs in an antiparallel configuration. A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonculeotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

A "base-specific intracellular binding event involving a target RNA" refers to the specific binding of an oligonucleotide analog to a target RNA sequence inside a cell. The base specificity of such binding is sequence specific. For example, a single-stranded polynucleotide can specifically bind to a single-stranded polynucleotide that is complementary in sequence.

An "effective amount" of an antisense oligomer, targeted against an infecting picornavirus, is an amount effective to reduce the rate of replication of the infecting virus, and/or viral load, and/or symptoms associated with the viral infection.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide analog preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. The analog also may be conjugated, e.g., at its 5' or 3' end, to an arginine-rich peptide, e.g., a portion of the HIV TAT protein, polyarginine, or combinations of arginine and other amino acids including the non-natural amino acids 6-aminohexanoic acid and beta-alanine. Exemplary arginine-rich delivery peptides are listed as SEQ ID NOS:15-20. These exemplary arginine-rich delivery peptides facilitate transport into the target host cell as described (Moulton, Nelson et al. 2004; Nelson, Stein et al. 2005).

Rules for the selection of targeting sequences capable of inhibiting replication of picornaviruses are discussed below.

II. Targeted Viruses

The present invention is based on the discovery that effective inhibition of members of the Picornaviridae family can be achieved with antisense oligonucleotide analog compounds that (i) target the region identified by SEQ ID NO: 4 of the 5' untranslated region (UTR) of the virus' positive strand, and (ii) have physical and pharmacokinetic features which allow effective interaction between the antisense compound and the virus within host cells. In one aspect, the oligomers can be used in treating a mammalian subject infected with the virus.

The invention targets single stranded, positive sense RNA viruses that are members of the Picornaviridae family. In particular, targeted viruses include members of the *Enterovirus* and *Rhinovirus* genera of the Picornaviridae family. Table 1 lists the viruses targeted by the invention as organized by genus. Various physical, morphological, and biological characteristics of members of the Picornaviridae family can be found, for example, in Textbook of Human Virology, R. Belshe, ed., 2nd Edition, Mosby, 1991, at the Universal Virus Database of the International Committee on Taxonomy of Viruses and in human virology textbooks (e.g., see Strauss and Strauss, 2002). Some of the key biological characteristics of the Picornaviridae family of viruses are described below.

TABLE 1

Targeted Viruses of the Invention

| Family | Genus | Virus |
|---|---|---|
| Picornaviridae | Enterovirus | Poliovirus (PV) |
| | | Human enterovirus A (HEV-A) |
| | | Human enterovirus B (HEV-B) |
| | | Human enterovirus C (HEV-C) |
| | | Human enterovirus D (HEV-D) |
| | Rhinovirus | Human Rhinovirus A (HRV-89) |
| | | Human Rhinovirus B (HRV-14) |

Picornaviruses

GenBank reference entries for exemplary viral nucleic acid sequences representing picornavirus genomic RNA are listed in Table 2 below. The nucleotide sequence numbers in Table 2 are derived from the Genbank reference for the positive-strand RNA. It will be appreciated that these sequence references are only illustrative of other sequences in the Picornaviridae family, as may be available from available gene-sequence databases or literature or patent resources.

Table 2 lists the target for a picornavirus genomic RNA region for a selection of clinically important picornaviruses. The target region is 32 nucleotides in length and contained within the internal ribosome entry site (IRES) domain of the 5' untranslated region (UTR). All the viruses listed in Table 2 are human isolates and are organized into the *Enterovirus* and *Rhinovirus* genera as *Human Enteroviruses A-D, Poliovirus, Rhinovirus A* and *Rhinovirus B* according to convention as provided by the International Committee on Taxonomy of Viruses (ICTV). The target sequences (SEQ ID NOS:1-3) are in the Sequence Listing table at the end of the specification.

An important feature of the present invention is the high degree of sequence conservation between viruses in the two genera, *Enterovirus* and *Rhinovirus*, as shown in FIG. 3. The prototypic member of the Picornaviridae family is poliovirus and the targeting sequences (described below) are made in reference to the poliovirus sequence. Table 2 lists the corresponding target regions in a number of clinically relevant Enteroviruses (*Enterovirus* Surveillance—United States, 200-2001. MMWR 2002;51:1047-1049.) and *Rhinoviruses*. The target homologies for the target region is shown in FIG. 3. The target sequence identified as SEQ ID NO:4 represents a combined target sequence, where the positions indicated by the letter "R" may be either A or G, and the position indicated by the letter "Y" may be either C or T in SEQ ID NOS:1-3.

TABLE 2

Exemplary Human Picornavirus Nucleic Acid Target Sequences 3'-32 Nucleotide Target Region

| Poliovirus-Mahoney strain | NC 002058 | V01149 | 531-562 | 1 |
|---|---|---|---|---|
| Enterovirus A (CV-A16) | NC 001612 | U05876 | 540-571 | 1 |
| Enterovirus 71 (HEV-71) | | U22521 | 536-567 | 1 |
| Enterovirus B (CV-B1) | NC 001472 | M16560 | 534-565 | 1 |

TABLE 2-continued

Exemplary Human Picornavirus Nucleic Acid Target Sequences 3'-32 Nucleotide Target Region

| Coxsackievirus B3 (CV-B3) | | M88483 | 535-566 | 1 |
|---|---|---|---|---|
| Coxsackievirus B2 (CV-B2) | | AF081485 | 536-567 | 1 |
| Coxsackievirus B4 (CV-B4) | | AF311939 | 537-568 | 1 |
| Coxsackievirus B5 (CV-B5) | | X67706 | 536-567 | 1 |
| Coxsackievirus A9 (CV-A9) | | D00627 | 536-567 | 1 |
| Echovirus 4 (EV-4) | | X89534 | 419-450 | 1 |
| Echovirus 6 (EV-6) | | U16283 | 534-565 | 1 |
| Echovirus 9 (EV-9) | | X92886 | 533-564 | 1 |
| Echovirus 11 (EV-11) | | X80059 | 537-568 | 1 |
| Echovirus 13 (EV-13) | | AY302539 | 535-566 | 1 |
| Echovirus 18 (EV-18) | | AF521513 | 94-125 | 1 |
| Echovirus 25 (EV-25) | | X90722 | 534-565 | 1 |
| Echovirus 30 (EV-30) | | AF311938 | 537-568 | 1 |
| Enterovirus C (CV-A21) | NC 001428 | D00538 | 529-560 | 1 |
| Enterovirus D (HEV-70) | NC 001430 | D00820 | 534-565 | 1 |
| Rhinovirus A (HRV-89) | NC 001617 | M16248 | 530-561 | 2 |
| Rhinovirus B (HRV-14) | NC 001490 | K02121 | 541-572 | 3 |

Targeting sequences are designed to hybridize to a region of the target sequence as listed in Table 3. Selected targeting sequences can be made shorter, e.g., 12 bases, or longer, e.g., 40 bases, and include a small number of mismatches, as long as the sequence is sufficiently complementary to hybridize with the target, and forms with the virus positive-strand, a heteroduplex having a Tm of 45° C. or greater.

More generally, the degree of complementarity between the target and targeting sequence is sufficient to form a stable duplex. The region of complementarity of the antisense oligomers with the target RNA sequence may be as short as 8-11 bases, but is preferably 12-15 bases or more, e.g. 12-20 bases, or 12-25 bases. An antisense oligomer of about 14-15 bases is generally long enough to have a unique complementary sequence in the viral genome. In addition, a minimum length of complementary bases may be required to achieve the requisite binding $T_m$, as discussed below.

Oligomers as long as 40 bases may be suitable, where at least a minimum number of bases, e.g., 12 bases, are complementary to the target sequence. In general, however, facilitated or active uptake in cells is optimized at oligomer lengths less than about 30, preferably less than 25. For PMO oligomers, described further below, an optimum balance of binding stability and uptake generally occurs at lengths of 15-22 bases.

The oligomer may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g., expression of viral protein(s), is modulated.

The oligomer may also incorporate guanine bases in place of adenine when the target nucleotide is a uracil residue. This is useful when the target sequence varies across different viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability. Although the target sequences shown in FIG. 3, and listed in Table 2 contain T for thymidine, which is the convention for sequence listings, it will be appreciated that because picornaviruses are RNA viruses, the T residues refer to uracil.

The stability of the duplex formed between the oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques. *Methods Enzymol*. Vol. 154 pp. 94-107. Each antisense oligomer should have a binding $T_m$, with respect to a complementary-sequence RNA, of greater than body temperature and preferably greater than 50 C. $T_m$'s in the range 60-80 C or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values.

The antisense activity of the oligomer may be enhanced by using a mixture of uncharged and cationic phosphorodiamidate linkages as shown in FIGS. 2G and 2H. The total number of cationic linkages in the oligomer can vary from 1 to 10, and be interspersed throughout the oligomer. Preferably the number of charged linkages is at least 2 and no more than half the total backbone linkages, e.g., between 2-8 positively charged linkages, and preferably each charged linkages is separated along the backbone by at least one, preferably at least two uncharged linkages. The antisense activity of various oligomers can be measured in vitro by fusing the oligomer target region to the 5' end a reporter gene (e.g. firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

Table 3 below shows exemplary targeting sequences, in a 5'-to-3' orientation, that are complementary to a broad spectrum of picornaviruses, specifically members of the *Enterovirus* and *Rhinovirus* genera. The targeting sequences listed below in Table 3 provide a collection of targeting sequences from which additional targeting sequences may be selected, according to the general class rules discussed above.

TABLE 3

Exemplary Antisense Oligomer Targeting Sequences

| PMO | Target Nucleotides | GenBank Acc. No. | Targeting Antisense Oligomer (5' to 3') | SEQ. ID NO. |
|---|---|---|---|---|
| 3'-32a | 531-562 | V00149 | GAAACACGGACACCCAAAGTAGTCGGTTCCGC | 5 |
| 3'-37 | 526-562 | V00149 | AAAANGAAACACGGACACCCAAAGTAGTCGGTTCCGC | 6 |
| PV533 | 533-552 | V00149 | CACCCAAAGTAGTCGGTTCC | 7 |
| PV539 | 539-558 | V00149 | CACGGACACCCAAAGTAGTC | 8 |
| PV544 | 544-562 | V00149 | GGAAACACGGACACCCAAAG | 9 |
| PV548 | 548-567 | V00149 | AAAAGGAAACACGGACACCC | 10 |
| CVB3-548 | 548-568 | M88483 | ATGAAACACGGACACCCAAAG | 11 |
| EnteroX | 541-562 | V00149 | GAAACACGGACACCCAAAGTAG | 12 |
| HRV14-IRES | 551-574 | K02121 | GAGAAACACGGACACCCAAAGTAG | 13 |
| CVB3-571 | 571-591 | M88483 | TAAGCAGCCAGTATAGGAATA | 14 |

III. Antisense Oligonucleotide Analog Compounds

A. Properties

As detailed above, the antisense oligonucleotide analog compound (the term "antisense" indicates that the compound is targeted against the virus' positive-sense strand RNA) has a base sequence targeting a region that includes one or more of the following; 1) the 5' untranslated region of the positive sense viral RNA and; 2) the internal ribosome entry site within the 5' untranslated region. In addition, the oligomer is able to effectively target infecting viruses, when administered to a host cell, e.g. in an infected mammalian subject. This requirement is met when the oligomer compound (a) has the ability to be actively taken up by mammalian cells, and (b) once taken up, form a duplex with the target RNA with a $T_m$ greater than about 45° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

B. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, and a comparable number of cationic linkages, such as N,N-diethylenediamine phosphoramidates (Dagle, Littig et al. 2000). The net charge is preferably neutral or at most 1-2 net charges per oligomer.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin (Feigner, Gadek et al. 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked covalently to the 5' or 3' end of the antisense oligomer. The peptide is typically 8-16 amino acids and consists of a mixture of arginine, and other amino acids including phenyalanine, cysteine, beta-alanine and 6-aminohexanoic acid. Exemplary arginine-rich delivery peptides are described in the Sequence Listing table as SEQ ID NOS:15-20. The use of arginine-rich peptide-PMO conjugates can be used to enhance cellular uptake of the antisense oligomer (See, e.g. Moulton, Nelson et al. 2004 and Moulton, Nelson et al. 2005).

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G.Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

C. Substantial Resistance to RNaseH

Two general mechanisms have been proposed to account for inhibition of expression by antisense oligonucleotides. (See e.g., (Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing or translation. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3'-P5' phosphoramidates (Ding, Grayaznov et al. 1996; Gee, Robbins et al. 1998).

A test oligomer can be assayed for its RNaseH resistance by forming an RNA:oligomer duplex with the test compound, then incubating the duplex with RNaseH under a standard assay conditions, as described in Stein et al. After exposure to RNaseH, the presence or absence of intact duplex can be monitored by gel electrophoresis or mass spectrometry.

D. In Vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent application Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as those regions of picornavirus RNA, as described above) the method can be used to detect the presence of a given picornavirus virus, or reduction in the amount of virus during a treatment method.

E. Exemplary Oligomer Backbones

Examples of nonionic linkages that may be used in oligo-nucleotide analogs are shown in FIGS. 2A-2G. In these figures, B represents a purine or pyrimidine base-pairing moiety effective to bind, by base-specific hydrogen bonding, to a base in a polynucleotide, preferably selected from adenine, cytosine, guanine, thymidine and uracil. Suitable backbone structures include carbonate (2A, R=O) and carbamate (2A, R=NH$_2$) linkages (Mertes and Coats 1969; Gait, Jones et al. 1974); alkyl phosphonate and phosphotriester linkages (2B, R=alkyl or —O-alkyl) (Lesnikowski, Jaworska et al. 1990); amide linkages (2C) (Blommers, Pieles et al. 1994); sulfone and sulfonamide linkages (2D, R$_1$, R$_2$=CH$_2$); and a thioformacetyl linkage (2E) (Cross, Rice et al. 1997). The latter is reported to have enhanced duplex and triplex stability with respect to phosphorothioate antisense compounds (Cross, Rice et al. 1997). Also reported are the 3'-methylene-N-methylhydroxyamino compounds of structure 2F. Also shown is a cationic linkage in FIG. 2H wherein the nitrogen pendant to the phosphate atom in the linkage of FIG. 2G is replaced with a 1-piperazino structure. The method for synthesizing the 1-piperazino group linkages is described below with respect to FIG. 11.

As noted above, the substantially uncharged oligomer may advantageously include a limited number of charged backbone linkages. One example of a cationic charged phophordiamidate linkage is shown in FIG. 2H. This linkage, in which the dimethylamino group shown in FIG. 2G is replaced by a 1-piperazino group as shown in FIG. 2G, can be substituted for any linkage(s) in the oligomer. By including between two to eight such cationic linkages, and more generally, at least two and no more than about half the total number of linkages interspersed along the backbone of the otherwise uncharged oligomer, antisense activity can be enhanced without a significant loss of specificity. The charged linkages are preferably separated in the backbone by at least 1 and preferably 2 or more uncharged linkages.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 1A-1D. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of the oligomer:RNA heteroduplex to resist RNAse degradation.

Exemplary backbone structures for antisense oligonucleotides of the invention include the β-morpholino subunit types are also shown in FIGS. 1A-1D, each linked by an uncharged, phosphorus-containing subunit linkage. FIG. 1A shows a phosphorus-containing linkage which forms the five atom repeating-unit backbone, where the morpholino rings are linked by a 1-atom phosphoamide linkage. FIG. 1B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1C:
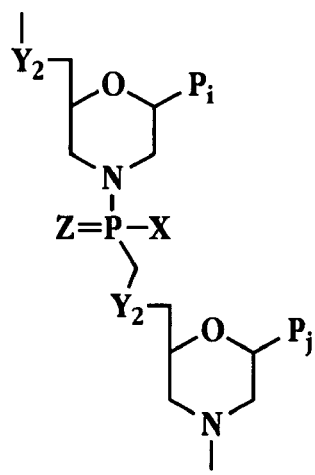
Figure 1D:
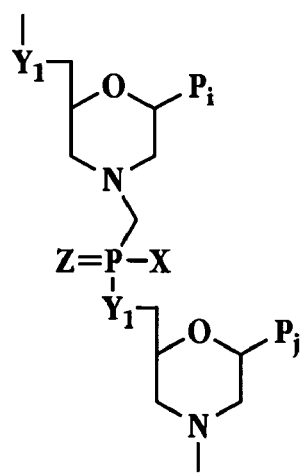

The linkages shown in FIGS. 1C and 1D are designed for 7-atom unit-length backbones. In Structure 1C, the X moiety is as in Structure 1B, and the moiety Y may be methylene, sulfur, or, preferably, oxygen. In Structure 1D, the X and Y moieties are as in Structure 1B. Particularly preferred morpholino oligonucleotides include those composed of morpholino subunit structures of the form shown in FIG. 1B, where X=NH$_2$ or N(CH$_3$)$_2$, Y=O, and Z=O and in FIG. 2G.

As noted above, the substantially uncharged oligomer may advantageously include a limited number of charged linkages, e.g. up to about 1 per every 5 uncharged linkages, more preferably up to about 1 per every 10 uncharged linkages. Therefore a small number of charged linkages, e.g. charged phosphoramidate or phosphorothioate, may also be incorporated into the oligomers. An exemplary cationic linkage structure is shown in FIG. 2H.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

IV. Inhibition of Picornavirus Viral Replication

The antisense compounds detailed above are useful in inhibiting replication of single-stranded, positive-sense RNA viruses of the Picornaviridae family. In one embodiment, such inhibition is effective in treating infection of a host animal by these viruses. Accordingly, the method comprises, in one embodiment, contacting a cell infected with the virus with an antisense agent effective to inhibit the replication of the specific virus. In this embodiment, the antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

In the present invention as described in the Examples, Phosphorodiamidate Morpholino Oligomers (PMOs), designed to hybridize to specific regions of the poliovirus 5' UTR, were evaluated for their ability to inhibit IRES-mediated translation in a cell-free translation system. Two regions that are highly conserved within the Picornaviridae family and even more highly conserved within the *Enterovirus* and *Rhinovirus* genera were specifically targeted. The data in the Examples also indicate that several of the PMOs tested in this study inhibit picornavirus replication in cell culture, specifically Coxsackievirus B3 (CVB3), and in vivo in a murine CVB3 infection model (e.g., see Example 5) and are potential picornavirus therapeutics.

However, the PMO described herein (SEQ ID NOS:5-13) will target most, if not all, picornavirus virus species because of the high degree of homology between virals species at the respective targets (SEQ ID NOS:1-3) as shown in FIG. 3.

A. Identification of the Infective Agent

The specific virus causing the infection can be determined by methods known in the art, e.g. serological, genotyping, or cultural methods, or by methods employing the antisense oligomers of the present invention.

Serological identification employs a viral sample or culture isolated from a biological specimen, e.g., stool, urine, cerebrospinal fluid, blood, nasopharyngeal secretions, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Genotyping methods include polymerase chain reaction (PCR) methods using genotype-specific primers or genomic sequencing of viral nucleic acid obtained from the infected individual.

Another method for identifying the viral infective agent in an infected subject employs one or more antisense oligomers targeting broad families and/or genera of viruses. Sequences targeting any characteristic viral RNA can be used. The desired target sequences are preferably (i) common to broad virus families/genera, and (ii) not found in humans. Characteristic nucleic acid sequences for a large number of infectious viruses are available in public databases, and may serve as the basis for the design of specific oligomers.

For each plurality of oligomers, the following steps are carried out: (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The virus is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of an antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically accepted carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligomer into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). As described above, the use of arginine-rich cellular delivery peptides conjugated to the antisense oligomer may also be used. Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc., and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 0.5 mg to 100 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

C. Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5):1157-1161, 1995; Anderson, K. P. et al., Antimicrob. Agents and Chemotherapy 40(9):2004-2011, 1996, Cottral, G. E. (ed) in: Manual of Standard Methods for Veterinary Microbiology, pp. 60-93, 1978).

A preferred method of monitoring the efficacy of the antisense oligomer treatment is by detection of the antisense-RNA heteroduplex. At selected time(s) after antisense oligomer administration, a body fluid is collected for detecting the presence and/or measuring the level of heteroduplex species in the sample. Typically, the body fluid sample is collected 3-24 hours after administration, preferably about 6-24 hours after administering. As indicated above, the body fluid sample may be urine, saliva, plasma, blood, spinal fluid, or other liquid sample of biological origin, and may include cells or cell fragments suspended therein, or the liquid medium and its solutes. The amount of sample collected is typically in the 0.1 to 10 ml range, preferably about 1 ml of less.

The sample may be treated to remove unwanted components and/or to treat the heteroduplex species in the sample to remove unwanted ssRNA overhang regions, e.g. by treatment with RNase. It is, of course, particularly important to remove overhang where heteroduplex detection relies on size separation, e.g., electrophoresis of mass spectroscopy.

A variety of methods are available for removing unwanted components from the sample. For example, since the heteroduplex has a net negative charge, electrophoretic or ion exchange techniques can be used to separate the heteroduplex from neutral or positively charged material. The sample may also be contacted with a solid support having a surface-bound antibody or other agent specifically able to bind the heteroduplex. After washing the support to remove unbound material, the heteroduplex can be released in substantially purified form for further analysis, e.g., by electrophoresis, mass spectroscopy or immunoassay.

V. Examples

The following examples illustrate but are not intended in any way to limit the invention.

A. Materials and Methods

Standard recombinant DNA techniques were employed in all constructions, as described in Ausubel, F M et al., in *CURRENT PROTOCOLS IN MOLECULAR BIOLOGY*, John Wiley and Sons, Inc., Media, Pa., 1992 and Sambrook, J. et al., in *MOLECULAR CLONING: A LABORATORY MANUAL*, Cold Spring Harbor Laboratory Press, Cold Spring Harbor, N.Y., Vol. 2, 1989).

All peptides were custom synthesized by Global Peptide Services (Ft. Collins, Colo.) or at AVI BioPharma (Corvallis, Oreg.) and purified to >90% purity. Phosphorodiamidate morpholino oligomers (PMOs) were synthesized at AVI BioPharma in accordance with known methods, as described, for example, in (Summerton and Weller 1997) and U.S. Pat. No. 5,185,444.

For Examples 2-5 described below, PMO oligomers were conjugated at the 5' end with an arginine-rich peptide $(RXR)_4$ XB-PMO (where R is arginine, X is 6-aminohexanoic acid and B is beta-alanine; SEQ ID NO:16) to enhance cellular uptake as described (U.S. Patent Application 60/466,703 and (Moulton, Nelson et al. 2004; Nelson, Stein et al. 2005). This peptide is also called P007 and listed as SEQ ID NO:16 in the Sequence Listing table.

Peptide-Conjugated PMO Treatment and Viral Infection of Mice

For peptide-conjugated PMO (PPMO) treatment of mice in the absence of virus, 12 four-week-old A/J [$H-2^a$] mice (Jackson Laboratory) mice were randomized into 4 groups and injected intravenously via tail vein twice, at time t=0 and t=48 hours, with either 100, 150 or 200 µg PPMO-6 (CVB3-548; SEQ ID NO:11), or identical volume (200 µl) of PBS. All mice were observed for appearance and behavior and weighed daily, for seven days.

For the experiment with virus, 18 mice (same age and type as above) were randomized to three groups (6/group) and infected intraperitoneally with $10^5$ plaque forming units (pfu) of CVB3. Mice were administered a volume of 200 µl containing either 200 µg of PPMO in PBS or PBS alone intravenously via tail vein injection at 3 h before infection and then again on day 2 pi. All mice were sacrificed on day 7 pi, at which time the ventricular portions of the hearts were collected, and transversely sectioned into the apex, mid and basal portions for analysis. Apex portions were weighed, homogenized in DMEM, and diluted to 1 mg of tissue per ml. Mid portions were fixed in 10% formalin and used for histopathology.

Preparation of Morpholino Oligomers having Cationic Linkages

Figure 11:
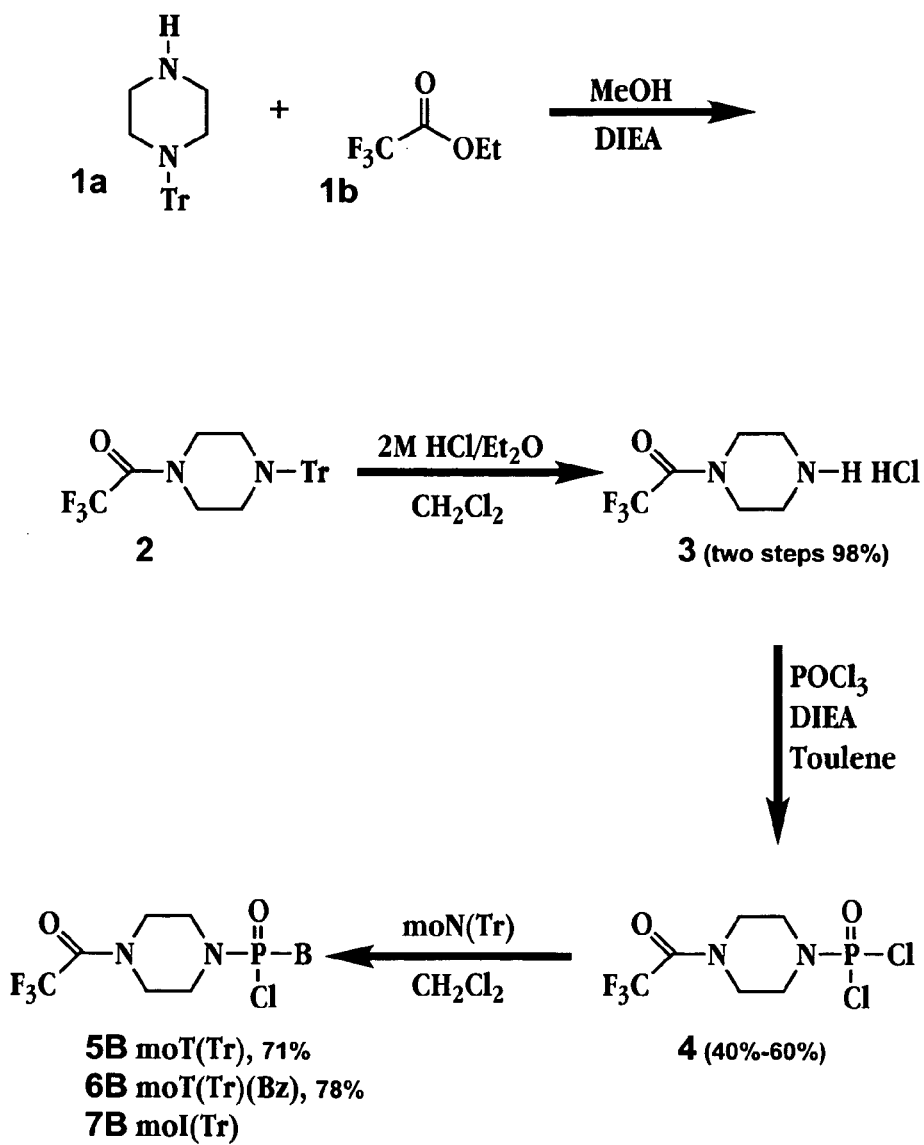
FIG. 11 shows the synthetic steps to produce subunits used to produce +PMO containing the (1-piperazino) phosphinylideneoxy cationic linkage as shown in FIG. 2H.

A schematic of a synthetic pathway that can be used to make morpholino subunits containing a (1 piperazino) phosphinylideneoxy linkage is shown in FIG. 11; further experimental detail for a representative synthesis is provided in Materials and Methods, below. As shown in the Figure, reaction of piperazine and trityl chloride gave trityl piperazine (1a), which was isolated as the succinate salt. Reaction with ethyl trifluoroacetate (1b) in the presence of a weak base (such as diisopropylethylamine or DIEA) provided 1-trifluoroacetyl-4-trityl piperazine (2), which was immediately reacted with HCl to provide the salt (3) in good yield. Introduction of the dichlorophosphoryl moiety was performed with phosphorus oxychloride in toluene.

The acid chloride (4) is reacted with morpholino subunits (moN), which may be prepared as described in U.S. Pat. No. 5,185,444 or in Summerton and Weller, 1997 (cited above), to provide the activated subunits (5,6,7). Suitable protecting groups are used for the nucleoside bases, where necessary; for example, benzoyl for adenine and cytosine, isobutyryl for guanine, and pivaloylmethyl for inosine. The subunits containing the (1 piperazino) phosphinylideneoxy linkage can be incorporated into the existing PMO synthesis protocol, as described, for example in Summerton and Weller (1997), without modification.

B. Example 1

Figure 4:
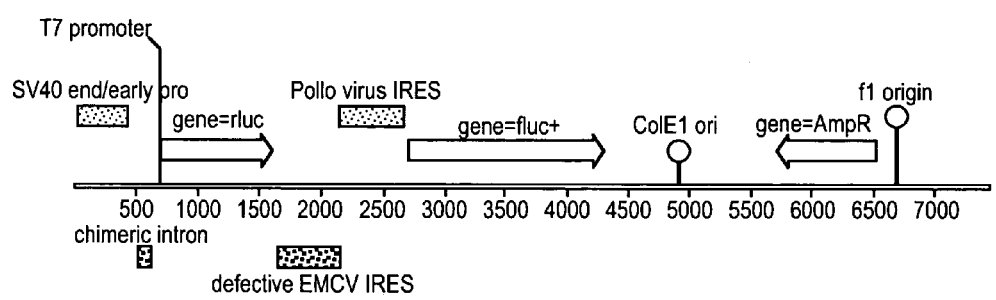
FIG. 4 shows a genetic map of the dual luciferase reporter construct pR&Fluc-PolioIRES.

Inhibition of Picornavirus virus RNA Translation with Phosphorodiamidate Morpholino Oligomers Phosphorodiamidate Morpholino Oligomers (PMOs), designed to hybridize to specific regions of the poliovirus internal ribosome entry site (IRES) region of poliovirus, as described above, were evaluated for their ability to inhibit translation in a rabbit reticulcyte lysate (RRL) assay. A dual reporter expression plasmid construct was derived as follows. A 507 nucleotide fragment of the 5' untranslated region of the poliovirus genome (ncts 124 to 630, GenBank No. V01149) was synthesized (BlueHeron, Inc) and inserted into the intercistronic region of a dual luciferase reporter plasmid described previously (Johannes, Carter et al. 1999; Wilson, Powell et al. 2000; Brasey, Lopez-Lastra et al. 2003) and named herein as pR&Fluc. The resulting plasmid, pR&Fluc-PolioIRES is shown schematically in FIG. 4. For transcription in vitro, the dicistronic luciferase pR&Fluc-PolioIRES construct was digested with BamHI and linear DNA was transcribed with T7 RNA polymerase using the RiboMAX protocol (Promega, Inc). Uncapped dicistronic RNAs were translated in the RRL, as recommended, and products of translation reactions were measured enzymatically using the dual luciferase reporter assay system (Promega).

Prior to cell-free translation, one nanomolar of the dicistronic RNA was incubated with PMOs (SEQ ID NOS:5-14) at varying concentrations ranging from 0.01 to 10 micromolar. Relative inhibiton of the fLuc downstream reporter gene was measured using a fluorometer.

C. Example 2

Inhibition of Coxsackievirus B3 (CVB3) in Tissue Culture with PMOs that Target the 5' UTR of CVB3

The antiviral activity of CVB3-specific PMOs was determined by measuring viral protein expression in PMO-treated, CVB3-infected cells. The test was performed on either cardiomyocytes (HL-1 cells) or HeLa cells. Cell monolayers (6-well plates) were seeded 16 to 20 hours prior to treatment with PMO or infection with virus. Serum-containing medium was replaced with serum-free medium during PMO treatment and infection. The infection is allowed to proceed for either 7 h or 24 h at 37° C. prior to collection of cells and the preparation of cell lysates for immunoblot detection of viral capsid protein by Western blot (i.e. immunoblot) assay using a polyclonall antibody to the CVB3 VP1 gene. Antisera against beta-actin was included as a loading control.

Figure 5A:
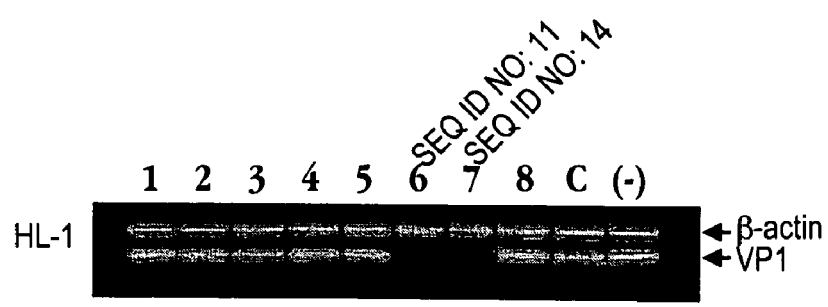
FIGS. 5A-5C show Western immunoblots of lysates from Coxsackievirus B3-infected cells treated with various antisense PMO compounds targeting CVB3.
Figure 5B:
Figure 5C:

In one set of experiments, $6 \times 10^5$ HL-1 cells (cardiomyocytes) were seeded in 6-well plates for 16-20 h. Culture medium was then replaced with serum-free medium and incubated with individual PMOs at final concentration of 10 µM. Four hours post-infection, cells were infected with CVB3 at a multiplicity of infection (MOI) of 10. At 24 hours post-infection, cell lysates were collected for Western immunoblot analysis to detect viral capsid protein VP1. The results are shown in FIG. 5A. Immunological detection of beta-actin was used as a loading control. Eight different peptide(P007)-conjugated PMOs were tested as shown in FIGS. 5A-5C. PMO compounds numbered 1-5 and 8 are directed to regions of the CVB3 genome not relevent to this invention. The compound "C" lane in FIG. 4 refers to a scrambled, negative control sequence and the lane labeled "(−)" refers to cells infected but not treated with any compound. Compounds 6 and 7 refer to CVB3-548 and CVB3-571, SEQ ID NOS:11 and 14, respectively. FIGS. 5B and 5C are Western immunoblots prepared under identical conditions using CVB3-infected HeLa cells in place of HL-1 cells. FIGS. 5B and 5C are results from cell lysates collected either seven hours or 24 hours post-infection, respectively. All other conditions are identical to those described for HL-1 cells except that $8 \times 10^5$ cells were seeded into the 6-well plates.

Figure 6A:
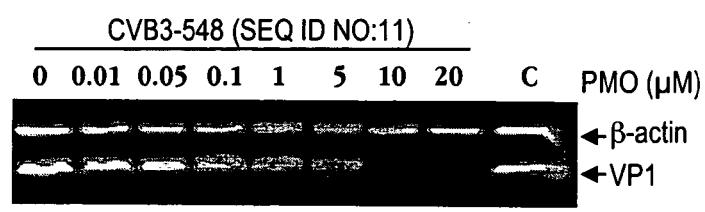
FIGS. 6A and 6B show a dose dependent antiviral effect of one PMO compound (PMO-6; SEQ ID NO:1) as measured using a Western immunoblot assay.
Figure 6B:
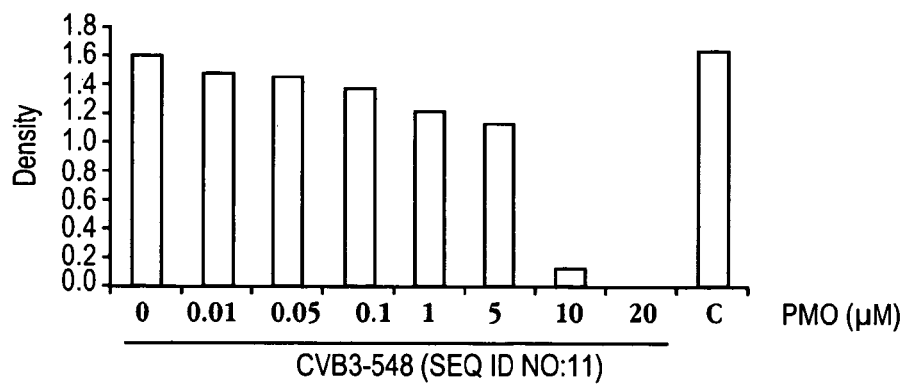

One of the effective antisense PMOs (PMO-6; CVB3-548; SEQ ID NO:11) was selected for a dose response assay using HeLa cells under the same conditions as described above for FIG. 5B. The results are shown as a Western immunoblot and density bar graph of the immunoblot signals in FIGS. 6A and 6B, respectively. The concentration range analyzed was from 0.01 to 20 micromolar PMO. Based on the results in FIG. 6B, an estimated effective concentration sufficient for a reduction in viral replication of 50% (EC50) for this PMO is between 5 and 10 micromolar.

Figure 7A:
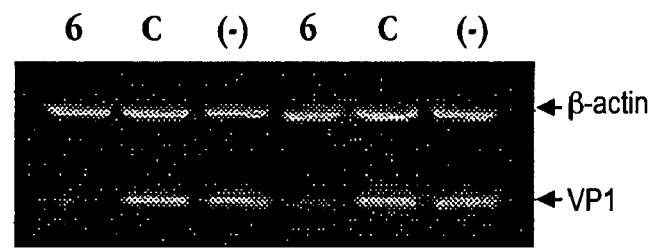
FIGS. 7A and 7B show the antiviral effect of one PMO compound (PMO-6; SEQ ID NO:11) when treatment was initiated one hour posit-CVB3 infection.
Figure 7B:
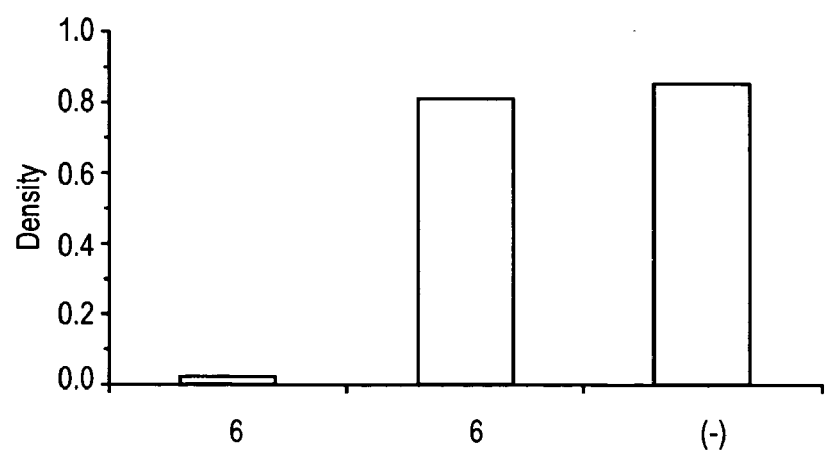

Effective inhibition of CVB3 replication with two PMOs was observed as described above and shown in FIGS. 5 to 6. This inhibition was under conditions where the PMO was introduced four hours prior to infection. An experiment identical to the conditions described for the results presented in FIGS. 5B and 5C was done except that the PMO was introduced into the cell culture one hour post-infection with CVB3. The results are shown as a Western immunoblot and density bar graph of the immunoblot signals in FIGS. 7A and 7B, respectively.

D. Example 3

Inhibition of CVB3-Induced Cytopathic Effects in Tissue Culture with PMOs that Target the 5' UTR of CVB3

Figure 8A:
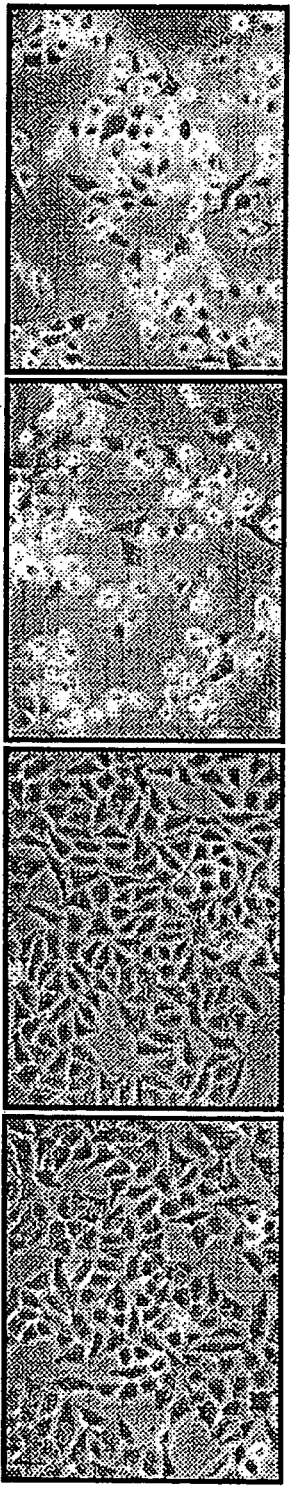
FIGS. 8A and 8B are photomicrographs that show two PMOs (PMOs-6 and -7; SEQ ID NOS:11 and 14) protect cardiomyocytes and HeLa cells from CVB3-induced cytopathic effects.
Figure 8B:
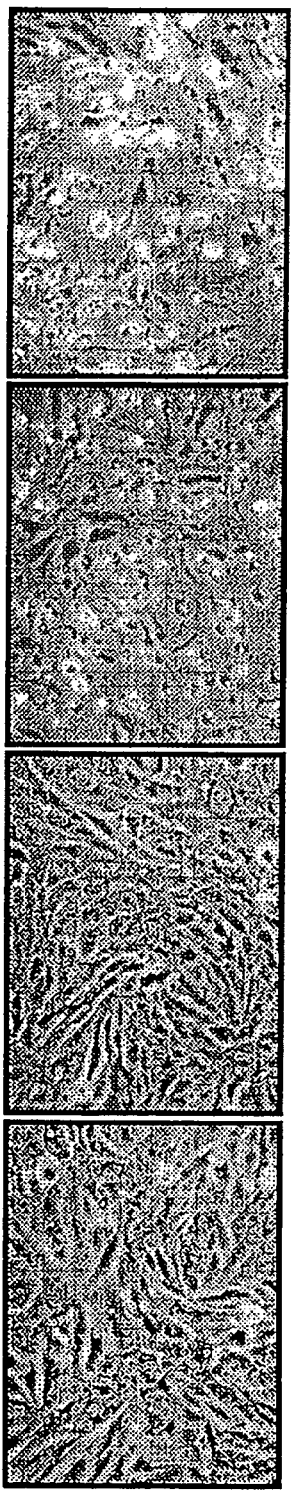

Another measure of antiviral activity is to observe a reduction in cytopathic effects (CPE) in tissue culture experiments. Two P007-conjugated PMO were selected for these analyses, CVB3-548 and CVB3-571 (compounds 6 and 7; SEQ ID NOS:11 and 14, respectively) were used to treat both HL-1 cells (cardiomyocytes) and HeLa cells under the same conditions described in Example 2 above. Four hours post-treatment with PMO, cells were infected with CVB3 at an MOI of ten. Photomicrographs were taken 24 hours post-infection for HeLa cells as shown in FIG. 8A and 40 hours post-infection for HL-1 cells as shown in FIG. 8B. The negative controls shown in FIGS. 8A and 8B were either no PMO or a P007-conjugated scramble control PMO (SCR). FIGS. 8A and 8B clearly demonstrate protection from CVB3-induced CPE in cultures treated with either compound 6 or 7 (CVB3-548 and CVB3-571; SEQ ID NOS:11 and 14, respectively) as compared to the scramble control PMO or no treatment.

E. Example 4

Inhibiton of HRV14, Poliovirus and CVB2 Replication in Tissue Culture with PMOs that Target the 5'-UTR of HRV14

Figure 9:
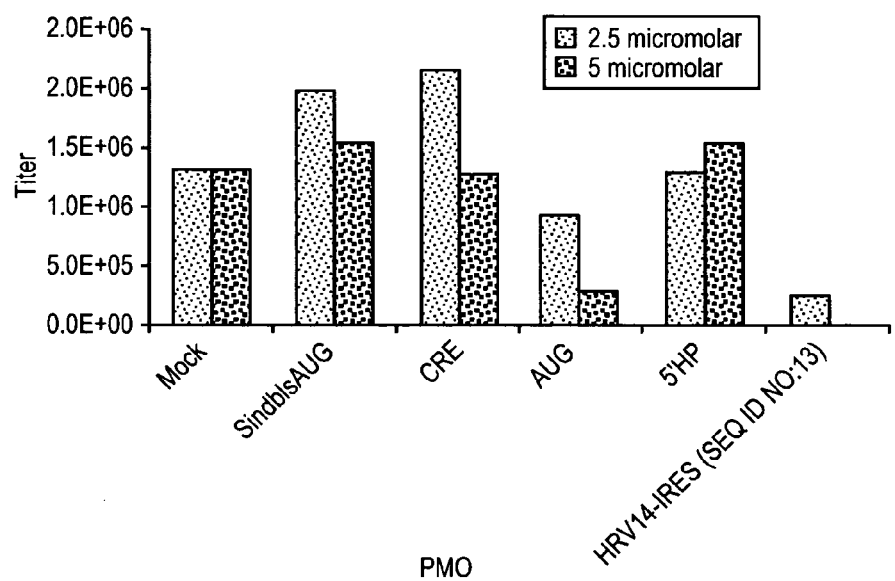
FIG. 9 shows the reduction of HRV-14 titer from cells treated with HRV14-IRES PMO (SEQ ID NO:13).

The ability of antisense PMO targeted to the IRES element within the 5'-UTR of Human rhinovirus 14 (HRV14) to inhibit replication HRV14, Poliovirus (PV) and Coxsackievirus B2 (CVB2) was determined by measuring the titer reduction in infected HeLa cells. HeLa cells were infected with HRV14 virus at an MOI of 0.03 and treated with the indicated PMOs shown in FIG. 9 for 24 hours. Media was harvested and the yield of virus was quantitated by plaque assay. FIG. 9 shows the effect of several PMOs targeted against HRV14 on the replication of HRV14 in HeLa cells as measure by titer reduction. The HRV14-IRES PMO (SEQ ID NO:13) is the only PMO of relevance to this invention. The SindbusAUG PMO serves as a negative control PMO. At both 2.5 and 5.0 micromolar PMO, the HRV14-IRES PMO significantly reduced the replication of HRV14.

Figure 10:
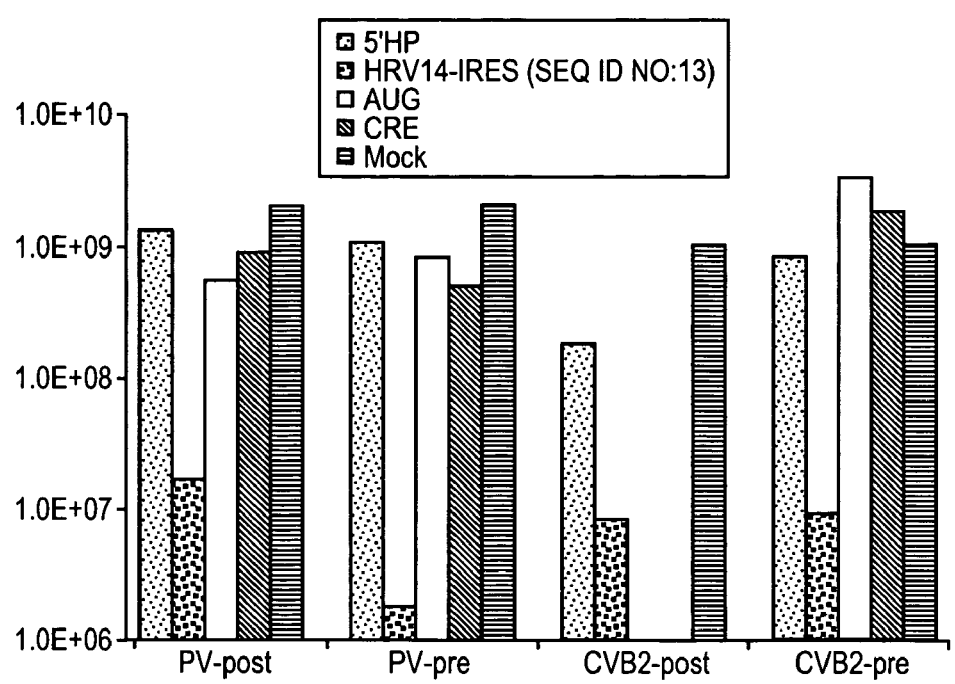
FIG. 10 shows the reduction of Poliovirus and Coxsackievirus B2 titer from cells treated with HRV14-IRES PMO (SEQ ID NO:13).

The same PMO (HRV14-IRES; SEQ ID NO:13) was used in a similar experiment to determine the antiviral activity against two other enteroviruses, Coxsackievirus B2 (CVB2) and Poliovirus (PV). FIG. 10 shows the antiviral effect of several PMO on the replication of these two viruses as measured by titer reduction. Two experimental conditions were used: 1) the PMO (5 micromolar) was used to treat the cells 4 hours pre-infection (PV-pre and CVB2-pre in FIG. 10) and; 2) at the time of infection (PV-post and CVB2-post in FIG. 10). The virus titer was measure two days post-infection. The AUG and CRE PMOs were not tested in the CVB2-post analysis. The HRV14-IRES PMO demonstrated an antiviral effect against both CVB2 and PV in these experiments as shown in FIG. 10.

F. Example 5

Peptide-Conjugated PMO Inhibits CVB3 Replication in Vivo and Attenuates the Severity of Murine Myocarditis Coxsackievirus B3 (CVB3), a member of the genus *Enterovirus* within the family Picornaviridae, is a primary causative agent of viral myocarditis. In North America, viral myocarditis accounts for 20% of sudden heart failure in children and adolescents. The chronic sequela of CVB3-induced myocarditis, dilated cardiomyopathy, is responsible for approximately 50% of cardiac transplants registered annually worldwide. Unfortunately, there is no specific therapeutic available to address CVB3-induced myocarditis, and as of this writing no clinical trials for such are registered through the FDA.

To determine a robust yet non-toxic dose of PPMO-6 (CVB3-548; SEQ ID NO:11 conjugated to P007; SEQ ID NO:16) for use in an in vivo CVB3 challenge, groups of mice (4 mice per group) were injected twice, with 100-200 µg of PPMO-6 per dose (or PBS), at 48 h apart, in the absence of virus. None of the dosages resulted in any evident toxicity throughout the ensuing seven day monitoring period. Daily weighing of all animals revealed no loss of average body weight in any of the groups (data not shown). Mice were observed daily and all displayed normal appearance (e.g. no ruffled fur) and behavior (e.g. no obvious lethargy). Histopathologic examination of heart, liver, kidney, spleen and pancreas revealed no abnormalities.

Figure 12A:
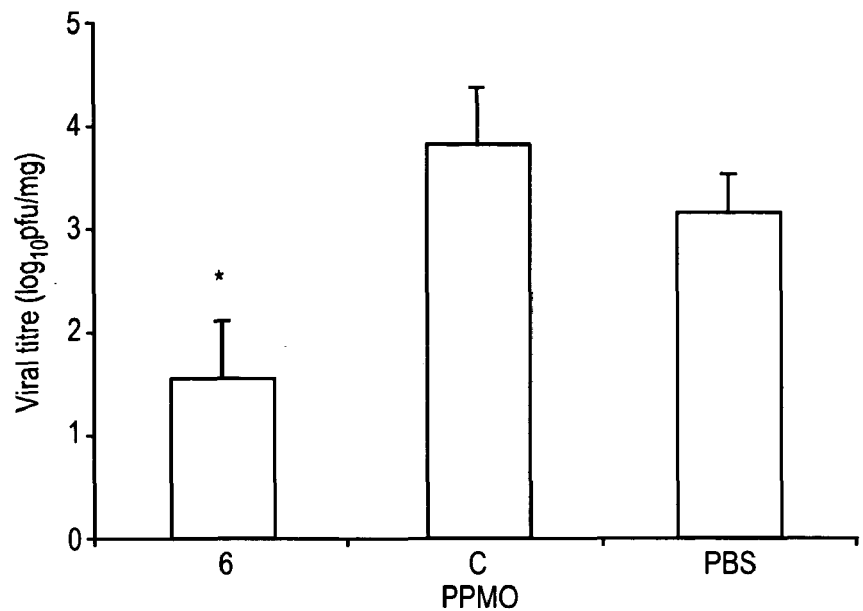
FIG. 12a shows the results of a CVB3 plaque assay of murine heart tissue after peptide-conjugated PMO (PPMO) treatment (PPMO-6; SEQ ID NO:11 conjugated to P007; SEQ ID NO:16) post-infection with CVB3.

Based on the preliminary dose vs. toxicity experiment, mice were randomized into three groups and each injected with 200 µg of PPMO-6, a negative control PPMO (PPMO-C) or PBS intravenously at 3 hours prior to CVB3 infection and then again 48 hours post-infection. Mice (n=6) subject to intravenous treatments of 200 µg with PPMO-6, PPMO-C, or PBS at 3 h before and 2 days after infection with $10^5$ pfu CVB3 were euthanized at day 7 pi, and organs harvested. The apical ventricular portion of hearts from each group were pooled and used for plaque assays. The titer difference between PPMO-6 and the controls (PPMO-C and PBS) was statistically significant (*P<0.05). Seven days post-infection, body weights were measured to determine virus-induced weight-loss, before euthanization. The average body weight loss of the PBS group was 17.44%, PPMO-C-treated was 15.82%, and the PPMO-6-treated was 12.55%. None of theses differences were statistically significant (P>0.05). For evaluation of the effect of PPMO treatment on CVB3 titers in the mouse hearts, plaque assays were performed on the pooled apex portions of the ventricles from each group. As shown in FIG. 12A, the amount of infectious virus particles in the tissue of the PPMO-6-treated group was approximately 2 $\log_{10}$ less than that in control groups (treated with either PPMO-C or PBS).

Figure 12B:
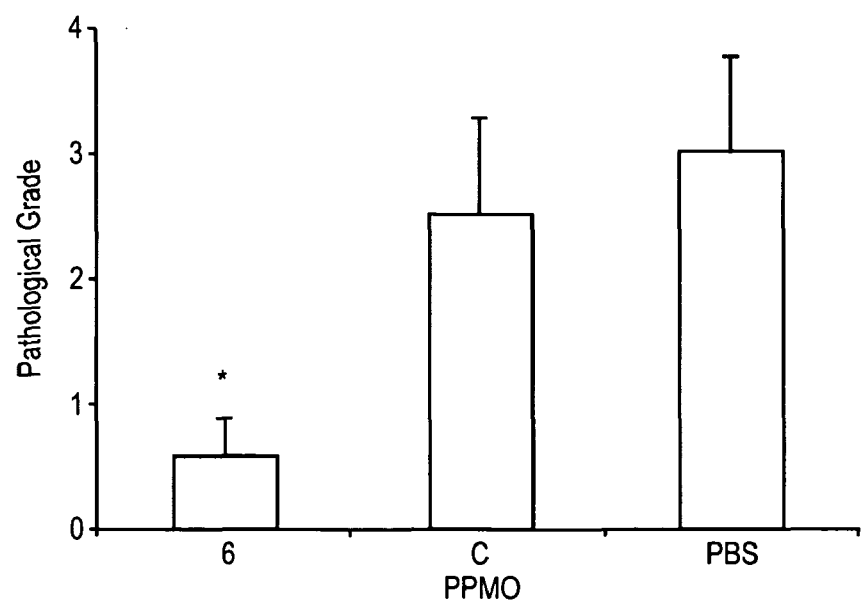
FIG. 12B shows the histopathology grading of heart tissue damage from the same mice.
Figure 13A:
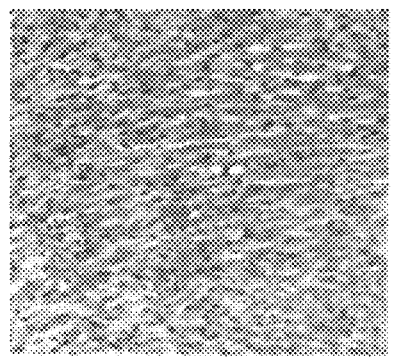
FIGS. 13A-D shows hematoxylin-eosin-stained heart tissue sections (200×), from (A) noninfected mice, or infected mice treated with (B) PPMO-6, (C) a negative control PPMO, or (D) PBS and demonstrates marked differences in CVB3-induced damage.
Figure 13B:
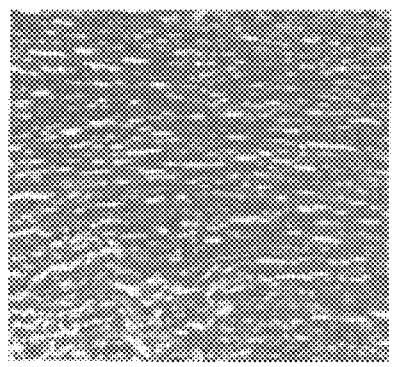
Figure 13C:
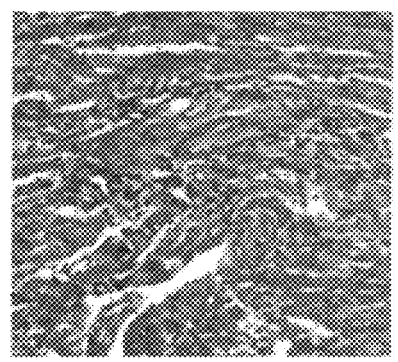
Figure 13D:
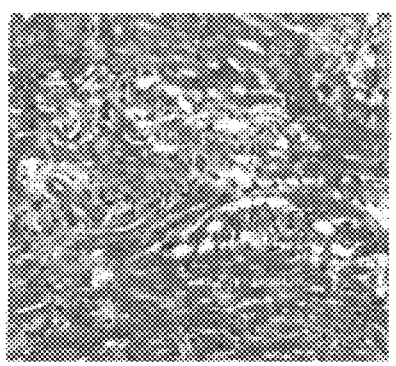

To examine whether this reduction of viral production in the myocardium was sufficient to attenuate the severity of myocarditis-associated tissue damage, the histopathology of stained mid-portion ventricular tissue sections was analyzed. The pathologic grade of myocarditis in PPMO-6-treated mice was significantly lower (*$P<0.05$) than in PPMO-C- or PBS-treated mice (FIG. 12B). Extensive myocardial infiltration of inflammatory cells and myocyte necrosis (grade 4-5) were observed in the PPMO-C- and PBS-treated mice (FIGS. 13C and 13D, respectively), whereas PPMO-6-treated mice had absent to mild (grade 0-1) tissue damage (FIG. 13B) similar to tissue from uninfected mice (FIG. 13A). These results show that heart tissue from noninfected mice and infected mice treated with PPMO-6 show marked differences in CVB3-induced damage compared to the negative control PPMO-C or PBS. Extensive inflammation and tissue damage is visible in PPMO-C- or PBS-treated compared to that of PPMO-6-treated or noninfected mice. In addition, the tissue damage to pancreas, liver, and spleen, as evaluated visually by microscopy of stained tissue slices, was far less in PPMO-6-treated mice than in the two control groups.

SEQUENCE LISTING

| Name | | SEQ ID NO |
|---|---|---|
| Target Sequences (5' to 3') | | |
| 3'-32 | GCGGAACCGACTACTTTGGGTGTCCGTGTTTC | 1 |
| 3'-32 | ATGGGACCAACTACTTTGGGTGTCCGTGTTTC | 2 |
| 3'-32 | ACGGGACCGACTACTTTGGGTGTCCGTGTTTC | 3 |
| 3'-32 | RYGGRACCRACTACTTTGGGTGTCCGTGTTTC | 4 |
| Oligomer Targeting Sequences (5' to 3') | | |
| 3'-32a | GAAACACGGACACCCAAAGTAGTCGGTTCCGC | 5 |
| 3'-37 | AAAANGAAACACGGACACCCAAAGTAGTCGGTTCCGC | 6 |
| PV533 | CACCCAAAGTAGTCGGTTCC | 7 |
| PV539 | CACGGACACCCAAAGTAGTC | 8 |
| PV544 | GGAAACACGGACACCCAAAG | 9 |
| PV548 | AAAAGGGAAACACGGACACCC | 10 |
| CVB3-548 | ATGAAACACGGACACCCAAAG | 11 |
| EnteroX | GAAACACGGACACCCAAAGTAG | 12 |
| HRV14-IRES | GAGAAACACGGACACCCAAAGTAG | 13 |
| CVB3-571 | TAAGCAGCCAGTATAGGAATA | 14 |
| Peptide Sequences (NH$_2$ to COOH) | | |
| P003 | RRRRRRRRRFFAhxβAla | 15 |
| P007 | (RAhxR)$_4$AhxβAla | 16 |
| P008 | (RAhx)$_8$βAla | 17 |
| RX4 | (RAhx)$_4$βAla | 18 |
| RXR2 | (RAhxR)$_2$AhxβAla | 19 |
| RXR3 | (RAhxR)$_3$AhxβAla | 20 |

It is claimed:

1. A method of treating an *Enterovirus* or *Rhinovirus* infection in a mammalian subject, comprising:

administering to the mammalian subject, a therapeutically effective amount of an antisense conjugate comprising:

an antisense oligonucleotide composed of between 20 and 40 morpholino subunits linked by phosphorous-containing intersubunit linkages which join a morpholino nitrogen of one subunit to a 5' exocyclic carbon of an adjacent subunit, and having a targeting sequence of at least 20 contiguous bases that are complementary to SEQ ID NO:4, and an arginine-rich carrier peptide conjugated to the antisense oligonucleotide, wherein the carrier peptide has the sequence of SEQ ID NO:16.

2. The method of claim 1, wherein the antisense conjugate forms a heteroduplex with at least 20 contiguous bases of SEQ ID NO: 4, wherein the heteroduplex has a Tm of dissociation of at least 45° C.

3. The method of claim 1, wherein the intersubunit linkages are uncharged.

4. The method of claim 1, wherein at least 2 and no more than half of the total number of intersubunit linkages of the antisense oligonucleotide are positively charged at physiological pH.

5. The method of claim 1, wherein the morpholino subunits are joined by intersubunit linkages in accordance with the structure:

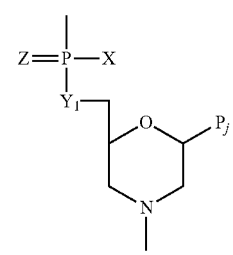

wherein $Y_1$=O, Z=O, Pj is a purine or pyrimidine base-pairing moiety effective to bind, by base-specific hydrogen bonding, to a base in a polynucleotide, and X is alkyl; alkoxy; thioalkoxy; 1-piperazine; or —$NR_2$, wherein each R is independently a hydrogen or methyl.

6. The method of claim 1, wherein the antisense oligonucleotide comprises at least 20 contiguous bases contained in SEQ ID NO:6.

7. The method of claim 6, wherein the antisense oligonucleotide sequence is selected from the group consisting of SEQ ID NOS:7, 8, 12 and 13.

8. The method of claim 1, further comprising administering an anti-viral composition to the mammalian subject.

9. The method of claim 1, wherein said administering is effective to reduce cardiopathology in a mammal infected with coxsackievirus B3.

10. The method of claim 1, wherein at least 2 and no more than half of the total number of intersubunit linkages of the antisense oligonucleotide contain a 1-piperazino group.

* * * * *